(12) United States Patent
Flaherty et al.

(10) Patent No.: US 6,939,305 B2
(45) Date of Patent: Sep. 6, 2005

(54) RAPID NON-INVASIVE BLOOD PRESSURE MEASURING DEVICE

(75) Inventors: Bryan Patrick Flaherty, Half Moon Bay, CA (US); Mark Henry Sher, San Francisco, CA (US); Richard G. Caro, San Francisco, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 10/685,068

(22) Filed: Oct. 14, 2003

(65) Prior Publication Data

US 2004/0077956 A1 Apr. 22, 2004

Related U.S. Application Data

(63) Continuation of application No. 09/412,295, filed on Oct. 5, 1999, now Pat. No. 6,632,181, which is a continuation of application No. 08/672,218, filed on Jun. 26, 1996, now Pat. No. 6,027,452.

(51) Int. Cl.$^7$ ................................. A61B 5/00
(52) U.S. Cl. ....................... 600/485; 600/500
(58) Field of Search ................. 600/500–503, 600/485, 490

(56) References Cited

U.S. PATENT DOCUMENTS

| | | | |
|---|---|---|---|
| 2,583,941 A | 1/1952 | Gordon, Jr. et al. | |
| 3,090,377 A | 5/1963 | Salisbury et al. | |
| 3,095,872 A | 7/1963 | Tolles | |
| 3,280,817 A | 10/1966 | Jorgensen et al. | |
| 3,318,303 A | 5/1967 | Hammacher | |
| 3,773,033 A | 11/1973 | Rodbard et al. | |
| 3,881,145 A | 4/1975 | Blick | |
| 3,885,551 A | 5/1975 | Massie | |
| 4,074,711 A | 2/1978 | Link et al. | |
| 4,141,350 A | 2/1979 | Shinoda | |

(Continued)

FOREIGN PATENT DOCUMENTS

| | | |
|---|---|---|
| CA | 1133211 | 1/1995 |
| CA | 2183638 | 2/2000 |
| EP | 0 443 267 | 12/1990 |
| JP | 4097738 | 3/1992 |
| JP | 2831471 | 9/1998 |
| WO | WO 86/04801 | 8/1986 |
| WO | WO 90/00029 | 1/1990 |
| WO | WO 90/05482 | 5/1990 |
| WO | WO 95/16391 | 6/1995 |
| WO | WO 95/28126 | 10/1995 |
| WO | WO 97/12545 | 5/1997 |

OTHER PUBLICATIONS

Shimazu et al.; "Vibration Technique for Indirect Measurement of Diastolic Arterial Pressure in Human Fingers"; Medical & Biological Engineering & Computing; Mar. 1989; pp. 130–136.

Gravlee, Glenn P., M.D. and Joni K. Brockschmidt; "Accuracy of Four Indirect Methods of Blood Pressure Measurement With Hemodynamic Correlations"; Journal of Clinical Monitoring; vol. 6, No. 4; Oct. 1990; pp. 284–298.

Ramsey, Maynard III, M.D., Ph.D.; "Blood Pressure Monitoring: Automated Oscillometric Devices"; Journal of Clinical Monitoring; vol. 7, No. 1; Jan. 1991; pp. 56–67.

(Continued)

*Primary Examiner*—Robert L. Nasser
(74) *Attorney, Agent, or Firm*—Knobbe, Martens, Olson & Bear, LLP

(57) ABSTRACT

A measurement device for generating an arterial volume-indicative signal includes an exciter and a detector. The exciter is adapted to receive an oscillating signal and generate a pressure wave based at least in part on the oscillating signal on the artery at a measurement site on a patient. The pressure wave includes a frequency. The detector is placed sufficiently near the measurement site to detect a volumetric signal indicative of arterial volume of the patient.

19 Claims, 18 Drawing Sheets

U.S. PATENT DOCUMENTS

| | | |
|---|---|---|
| 4,154,238 A | 5/1979 | Link |
| 4,172,450 A | 10/1979 | Rogers et al. |
| 4,181,134 A | 1/1980 | Mason et al. |
| 4,202,348 A | 5/1980 | Abe et al. |
| 4,203,451 A | 5/1980 | Panico |
| 4,250,894 A | 2/1981 | Frei et al. |
| 4,265,251 A | 5/1981 | Tickner |
| 4,269,193 A | 5/1981 | Eckerle |
| 4,295,471 A | 10/1981 | Kaspari |
| 4,307,728 A | 12/1981 | Albert |
| 4,343,314 A | 8/1982 | Sramek |
| 4,349,034 A * | 9/1982 | Ramsey, III ............ 600/494 |
| 4,406,289 A | 9/1983 | Wesseling et al. |
| 4,409,983 A | 10/1983 | Albert |
| 4,423,738 A | 1/1984 | Newgard |
| 4,443,730 A | 4/1984 | Kitamura et al. |
| 4,475,554 A | 10/1984 | Hyndman |
| 4,510,940 A | 4/1985 | Wesseling |
| 4,524,777 A | 6/1985 | Kisioka et al. |
| 4,539,997 A | 9/1985 | Wesseling et al. |
| 4,561,447 A | 12/1985 | Kawamura et al. |
| 4,562,843 A | 1/1986 | Djordjevich et al. |
| RE32,180 E | 6/1986 | Lewiner et al. |
| 4,646,754 A | 3/1987 | Seale |
| 4,660,566 A | 4/1987 | Palti |
| 4,669,485 A | 6/1987 | Russell |
| 4,699,152 A | 10/1987 | Link |
| 4,718,426 A | 1/1988 | Russell |
| 4,718,427 A | 1/1988 | Russell |
| 4,718,428 A | 1/1988 | Russell |
| 4,771,792 A | 9/1988 | Seale |
| 4,784,152 A | 11/1988 | Shinoda et al. |
| 4,791,915 A | 12/1988 | Barsotti et al. |
| 4,796,184 A | 1/1989 | Bahr et al. |
| 4,799,491 A | 1/1989 | Eckerle |
| 4,802,488 A | 2/1989 | Eckerle |
| 4,846,189 A | 7/1989 | Sun |
| 4,869,261 A | 9/1989 | Penaz |
| 4,873,987 A | 10/1989 | Djordjevich et al. |
| 4,907,596 A | 3/1990 | Schmid et al. |
| 4,924,871 A | 5/1990 | Honeyager |
| 4,960,128 A | 10/1990 | Gordon et al. |
| 5,033,471 A | 7/1991 | Yokoe et al. |
| 5,099,853 A | 3/1992 | Uemura et al. |
| 5,101,829 A | 4/1992 | Fujikawa et al. |
| 5,111,817 A | 5/1992 | Clark et al. |
| 5,148,807 A | 9/1992 | Hsu |
| 5,163,438 A | 11/1992 | Gordon et al. |
| 5,165,416 A | 11/1992 | Shinoda et al. |
| 5,237,997 A | 8/1993 | Greubel et al. |
| 5,241,963 A | 9/1993 | Shankar |
| 5,241,964 A | 9/1993 | McQuilkin |
| 5,261,414 A | 11/1993 | Aung et al. |
| 5,267,565 A | 12/1993 | Beard |
| 5,279,303 A | 1/1994 | Kawamura et al. |
| 5,309,916 A | 5/1994 | Hatschek |
| 5,337,750 A | 8/1994 | Walloch |
| 5,339,818 A | 8/1994 | Baker et al. |
| 5,385,149 A * | 1/1995 | Chang et al. ............ 600/493 |
| 5,390,679 A | 2/1995 | Martin |
| 5,394,877 A | 3/1995 | Orr et al. |
| 5,423,322 A | 6/1995 | Clark et al. |
| 5,425,372 A | 6/1995 | Takeda |
| 5,439,001 A | 8/1995 | Butterfield et al. |
| 5,447,163 A | 9/1995 | Apple |
| 5,494,043 A | 2/1996 | O'Sullivan et al. |
| 5,533,511 A | 7/1996 | Kaspari et al. |
| 5,551,440 A | 9/1996 | Miyawaki |
| 5,590,649 A | 1/1997 | Caro et al. |
| 5,634,467 A | 6/1997 | Nevo |
| 5,640,964 A | 6/1997 | Archibald et al. |
| 5,722,414 A | 3/1998 | Archibald et al. |
| 5,791,347 A | 8/1998 | Flaherty et al. |
| 5,807,268 A | 9/1998 | Reeves et al. |
| 5,810,734 A | 9/1998 | Caro et al. |
| 5,830,131 A | 11/1998 | Caro et al. |
| 5,833,618 A | 11/1998 | Caro et al. |
| 5,904,654 A | 5/1999 | Wohltmann et al. |
| 6,027,452 A | 2/2000 | Flaherty et al. |
| 6,045,509 A | 4/2000 | Caro et al. |

OTHER PUBLICATIONS

"Medwave: A New Choice Vasotrac™ APM 205 Blood Pressure Monitor" Brochure; Medwave, Inc.; 1995.

PCT International Search Report, App. No.: PCY/US95/04124, App. Date: Apr. 3, 1995, 3 pages.

M. Anliker et al., "Dispersion and Attenuation of Small Artificial Pressure Waves in the Canine Aorts," Circulation Research, vol. XXIII, 1968, pp. 539–551.

R. Cobbold, RF and Microwave Designer's Handbook, pp. 504–510, 766–776.

M. Landowne, "Characteristics of Impact and Pulse Wave Propagation in Brachial and Radial Arteries," Journal of Applied Physiology, vol. 12, pp. 1–97.

R.G. Pearl et al., "Continuous Non–Invasive Blood Pressure Measurement Using Arterial Pressure Wave Velocity," Stanford University School of Medicine, 1995.

J.D. Pruett et al., "Measurement of Pulse–Wave Velocity Using a Beat–Sampling Technique," L.A. Geddes, Annals of Biomedical Engineering. vol. 16, 1988, pp. 341–347.

Stanford Research Systems, "Application Note #3 About Lock–In Amplifier," Scientific and Engineering Instruments, 1992–1993, pp. 129–139.

Shimazu et al., "Electric Impedance Cuff for the Indirect Measurement of Blood Pressure and Volume Elastic Modulus in Human Limb and Finger Artieres," Medical Biological Engineering & Computing, vol. 27, Sep. 1989, pp. 477–483.

"Transducers for Biomedical Measurements; Principles and Applications," Institute of Biomedical Engineering, pp. 170–173.

PCT International Search Report, App. No.: PCT/US95/12452, App. Date: Nov. 20, 1995, 2 pages.

PCT International Search Report, App. No.: PCT/US96/15820, App. Date: Mar. 26, 1997, 3 pages.

PCT International Search Report, App. No.: PCT/US96/15879, App. Date: Dec. 7, 1996, 2 pages.

PCT International Search Report, App. No.: PCT/US96/15951, App. Date: Mar. 10, 1996, 5 pages.

PCT International Search Report, App. No.: PCT/US96/15956, App. Date: Jan. 7, 1997, 3 pages.

PCT International Search Report, App. No.: PCT/US97/10381, App. Date: Jun. 12, 1997, 3 pages.

PCT International Search Report, App. No.: PCT/US97/13743, App. Date: Oct. 17, 1997, 3 pages.

PCT International Search Report, App. No.: PCT/US00/30250, App. Date: Jan. 11, 2000, 3 pages.

* cited by examiner

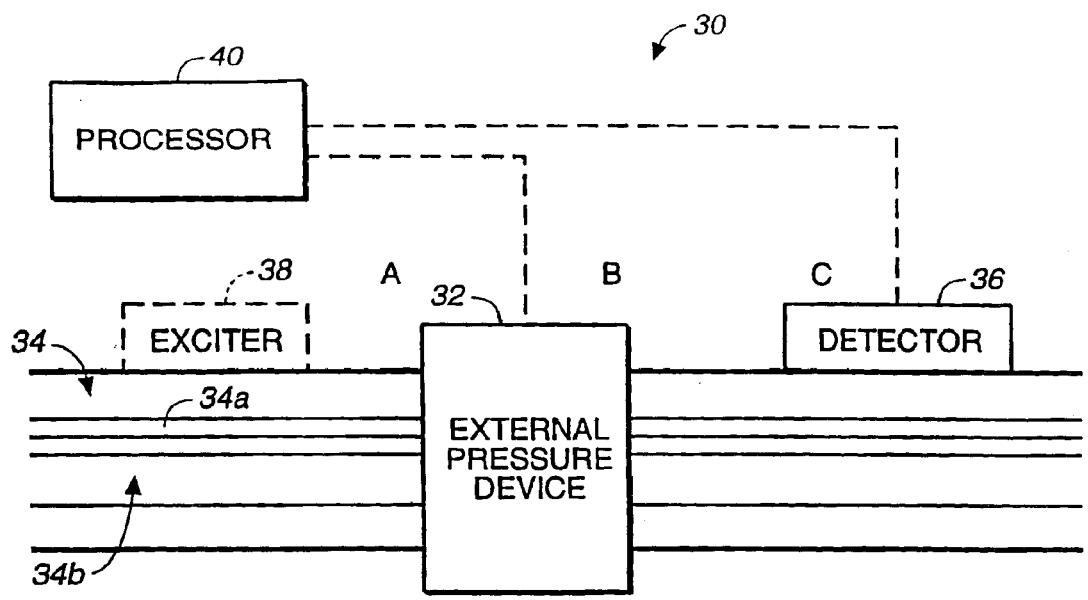
FIG._1
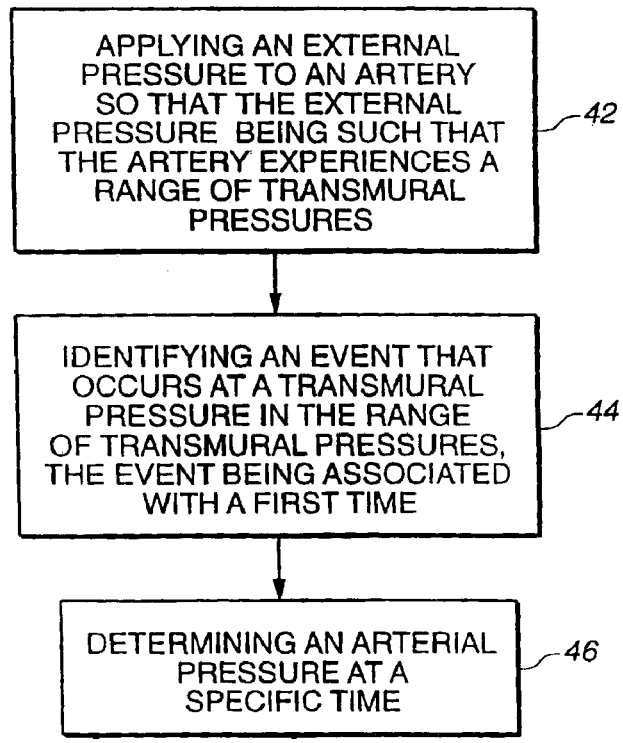
FIG._2

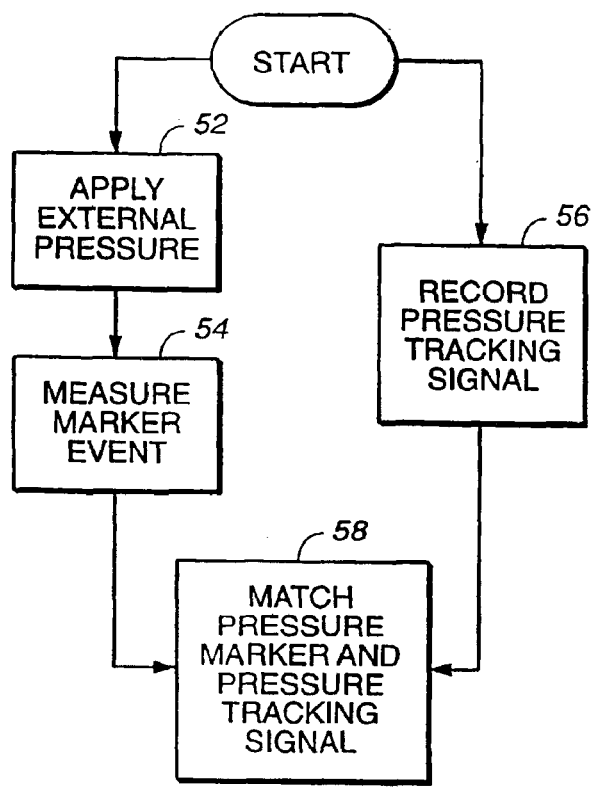
FIG._3
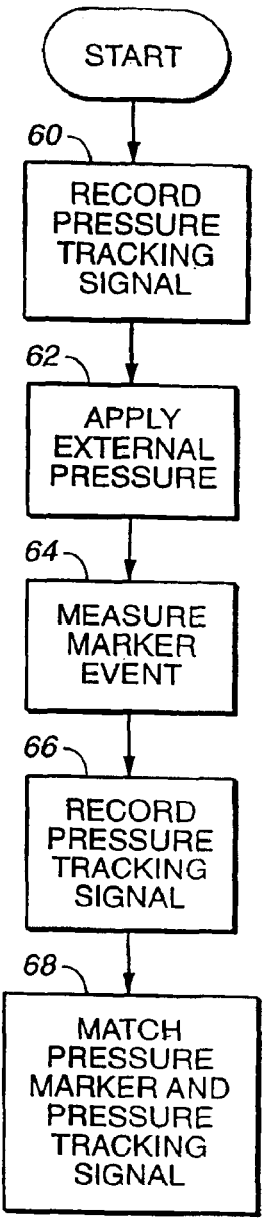
FIG._4

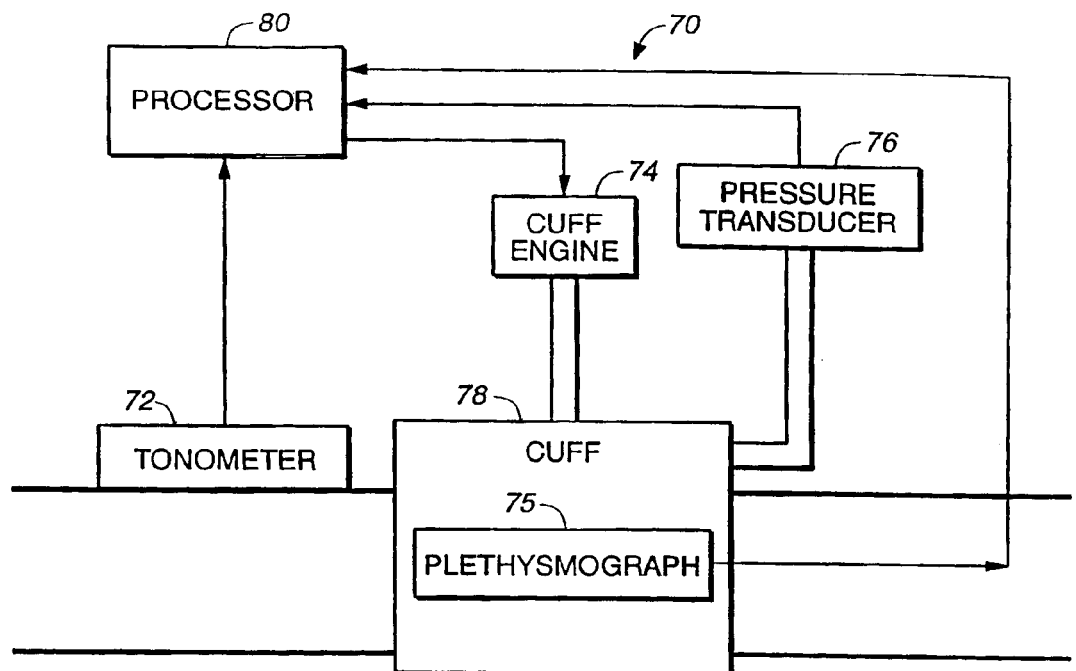
FIG._5
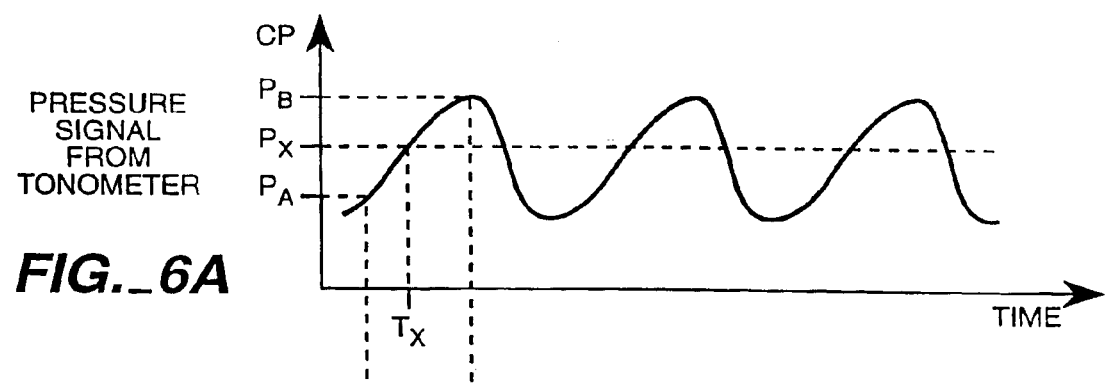
FIG._6A
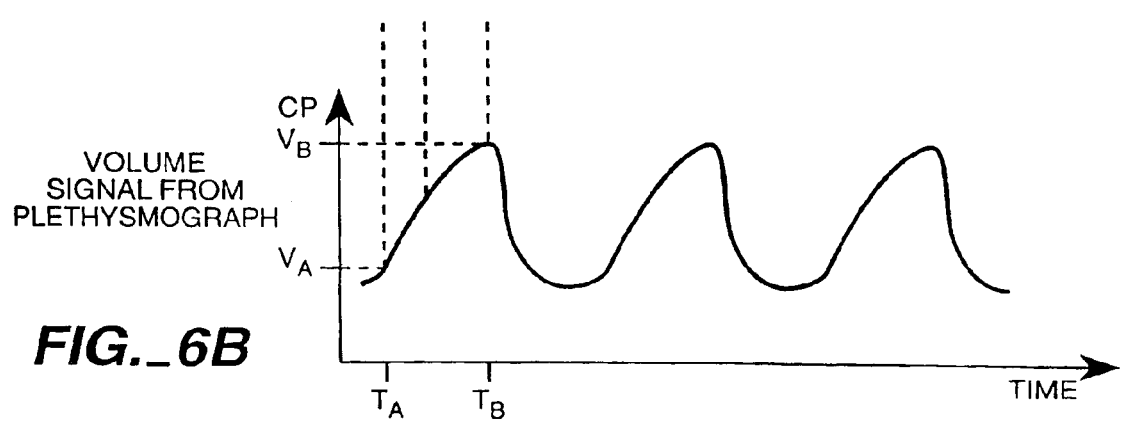
FIG._6B

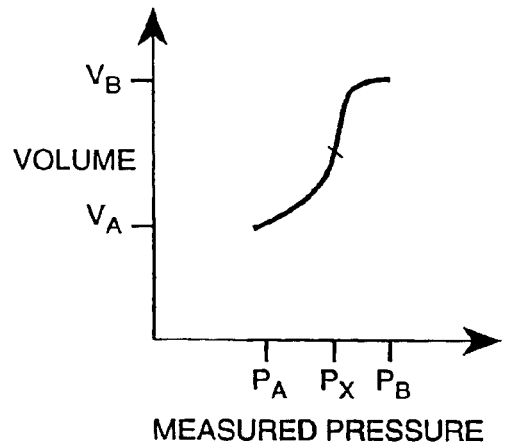
FIG._6C
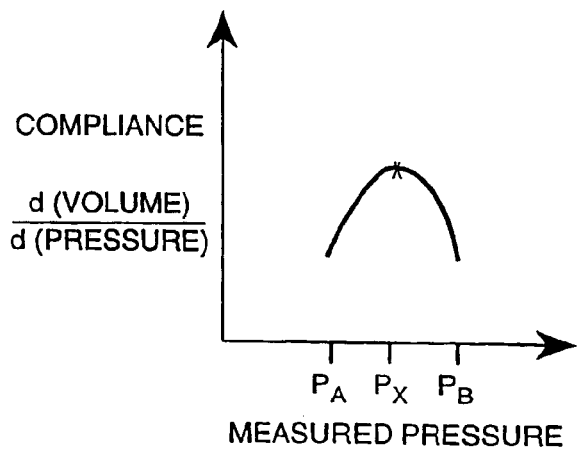
FIG._6D
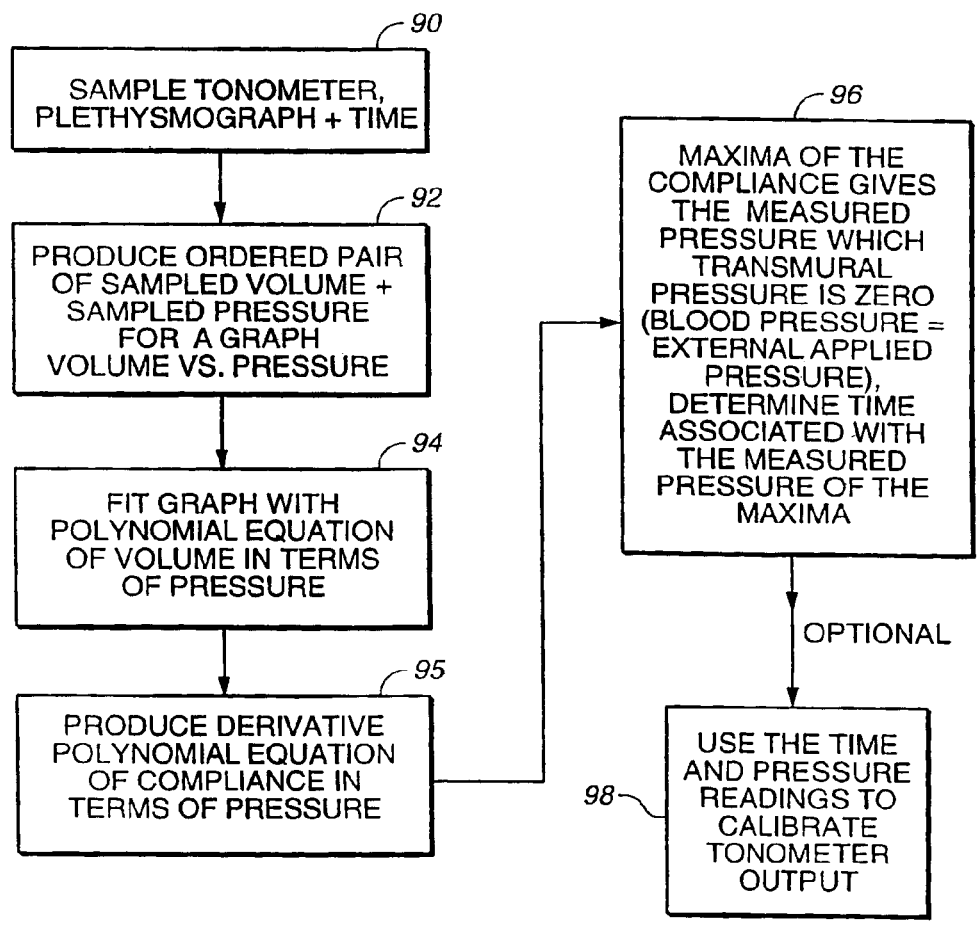
FIG._7

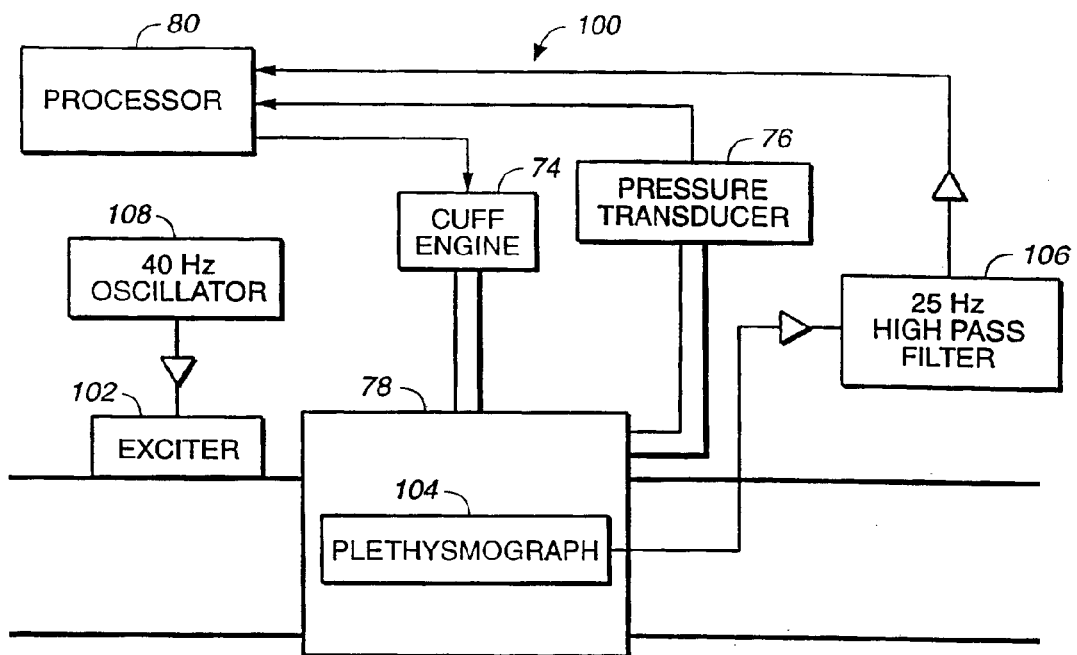
FIG._8
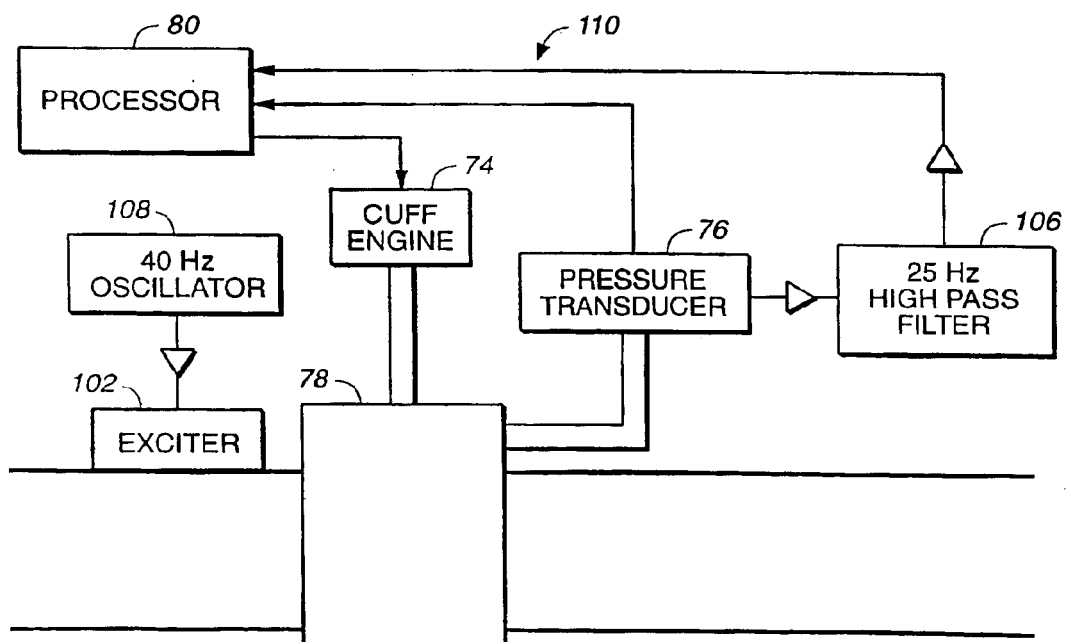
FIG._9

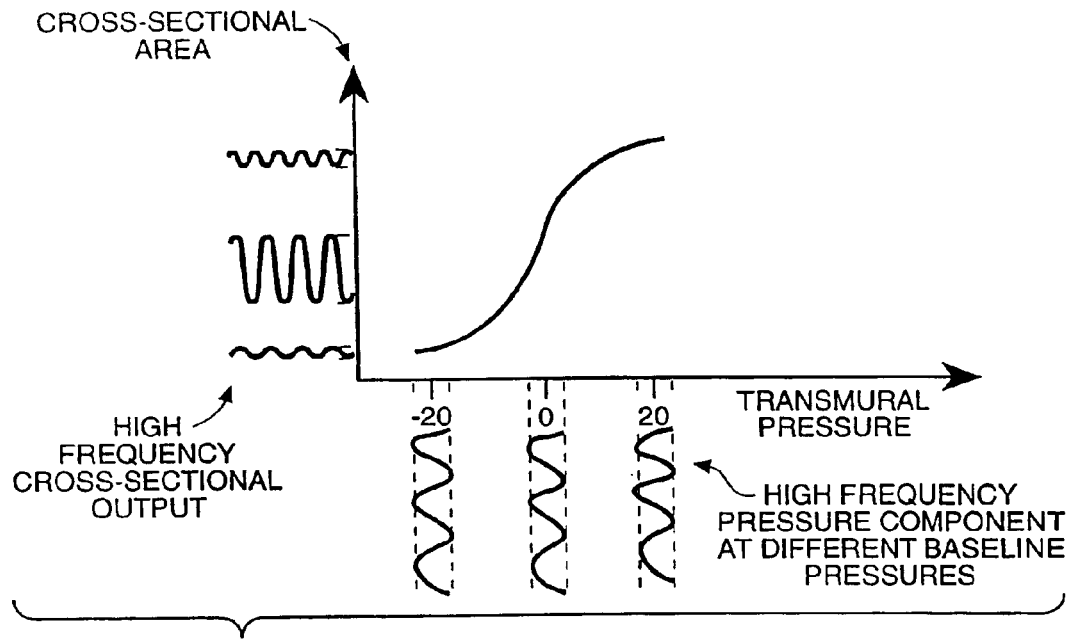
FIG._10
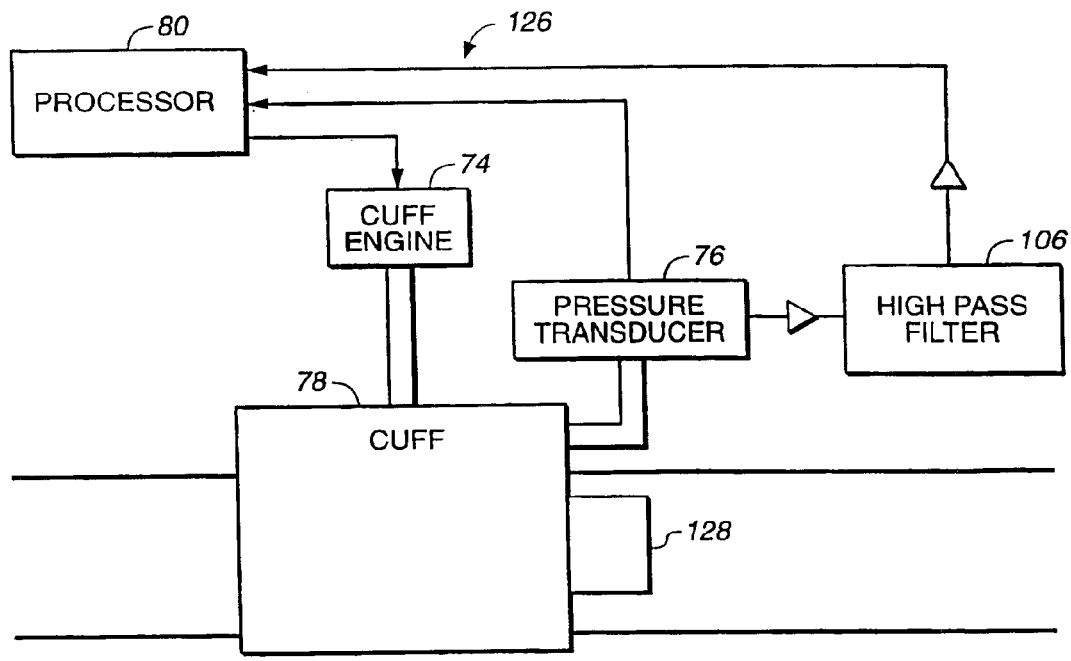
FIG._13

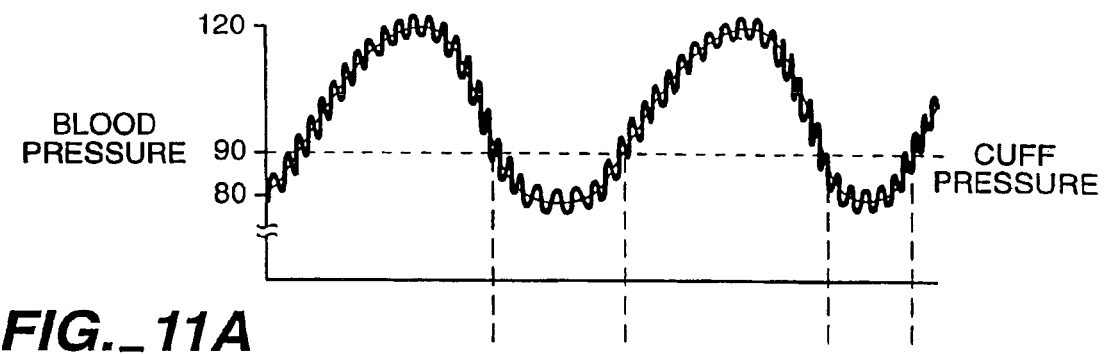
FIG._11A
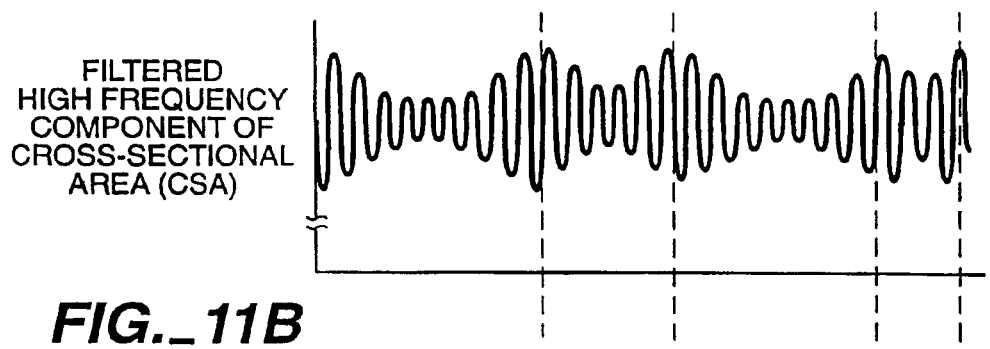
FIG._11B
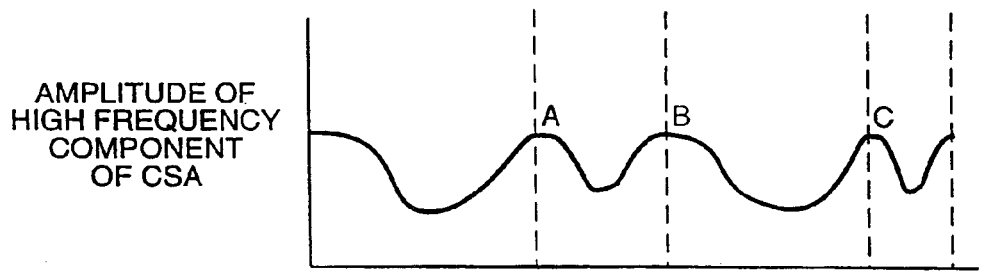
FIG._11C

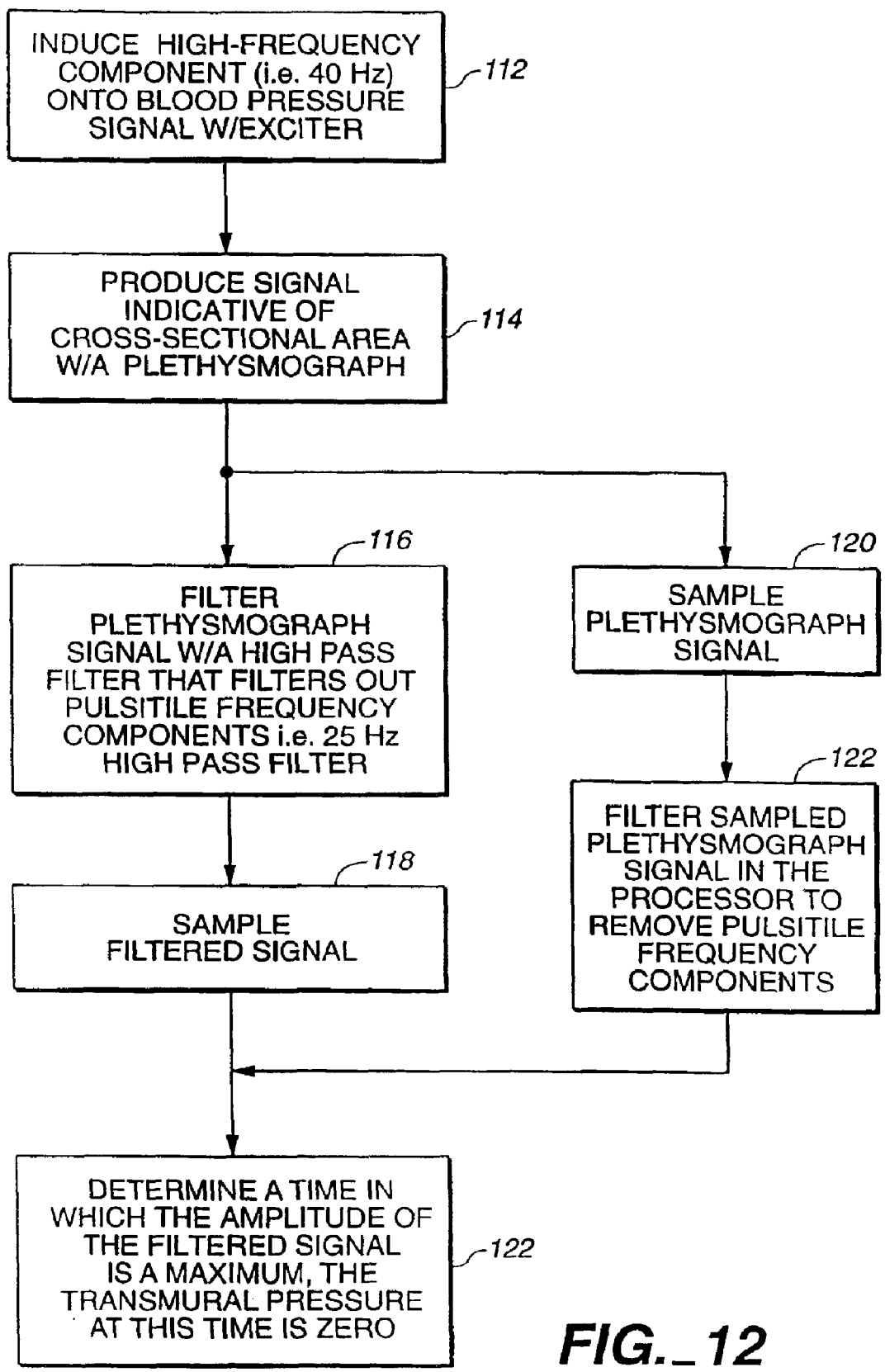
FIG._12

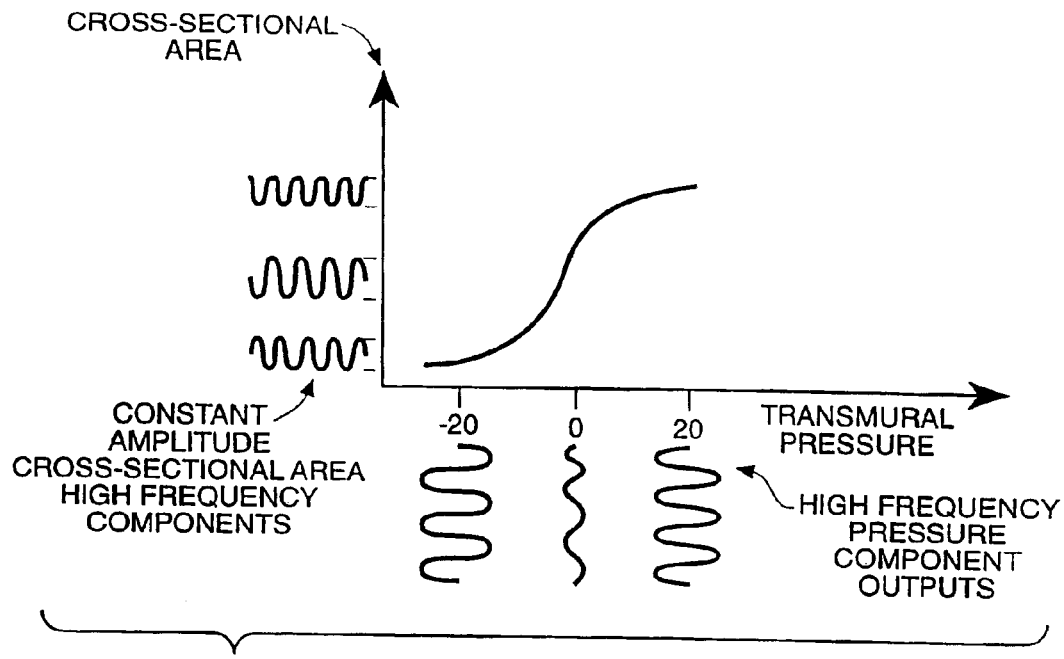
FIG._14
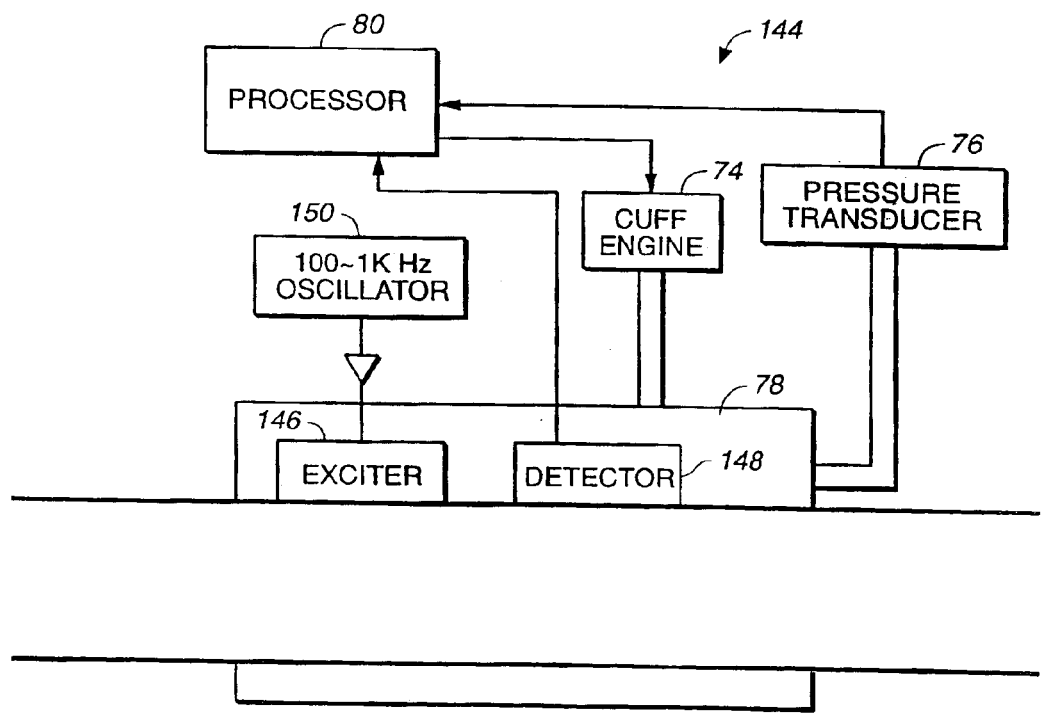
FIG._17

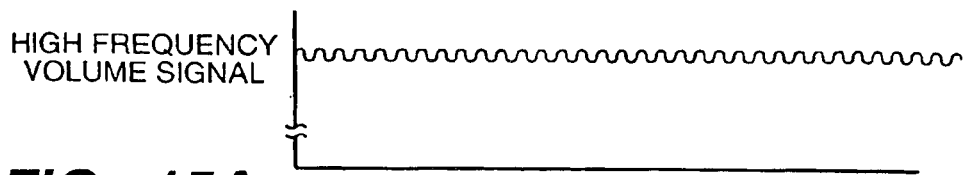
FIG._15A
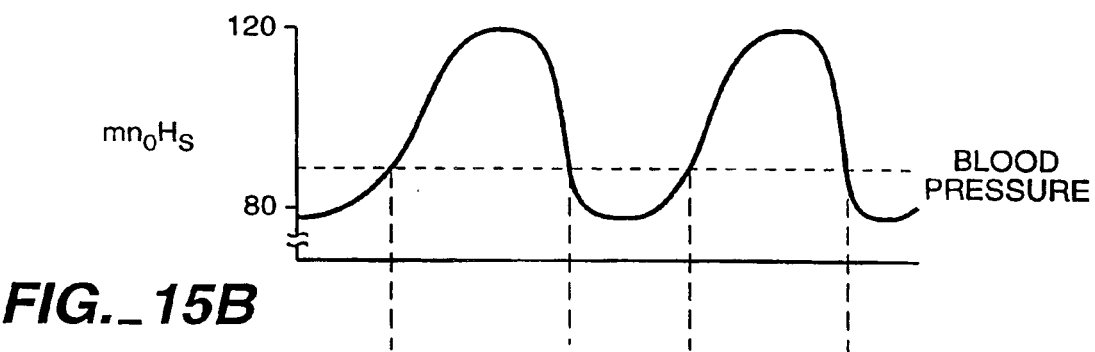
FIG._15B
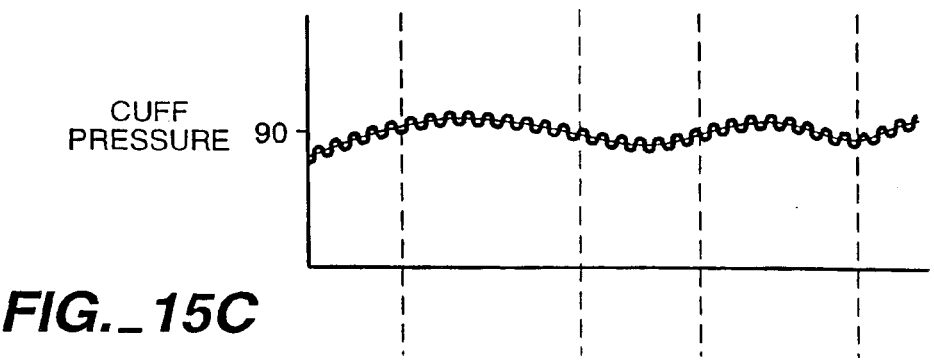
FIG._15C
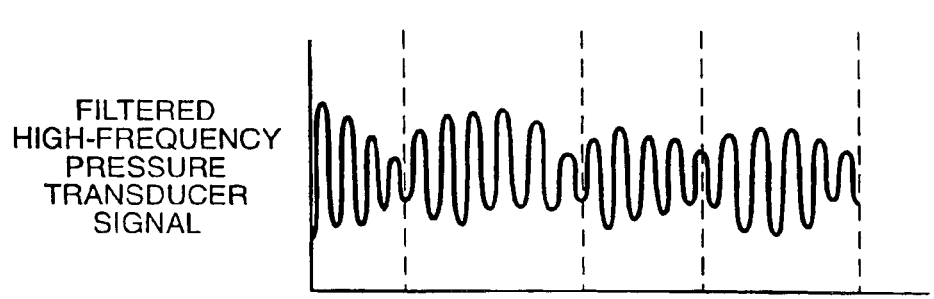
FIG._15D

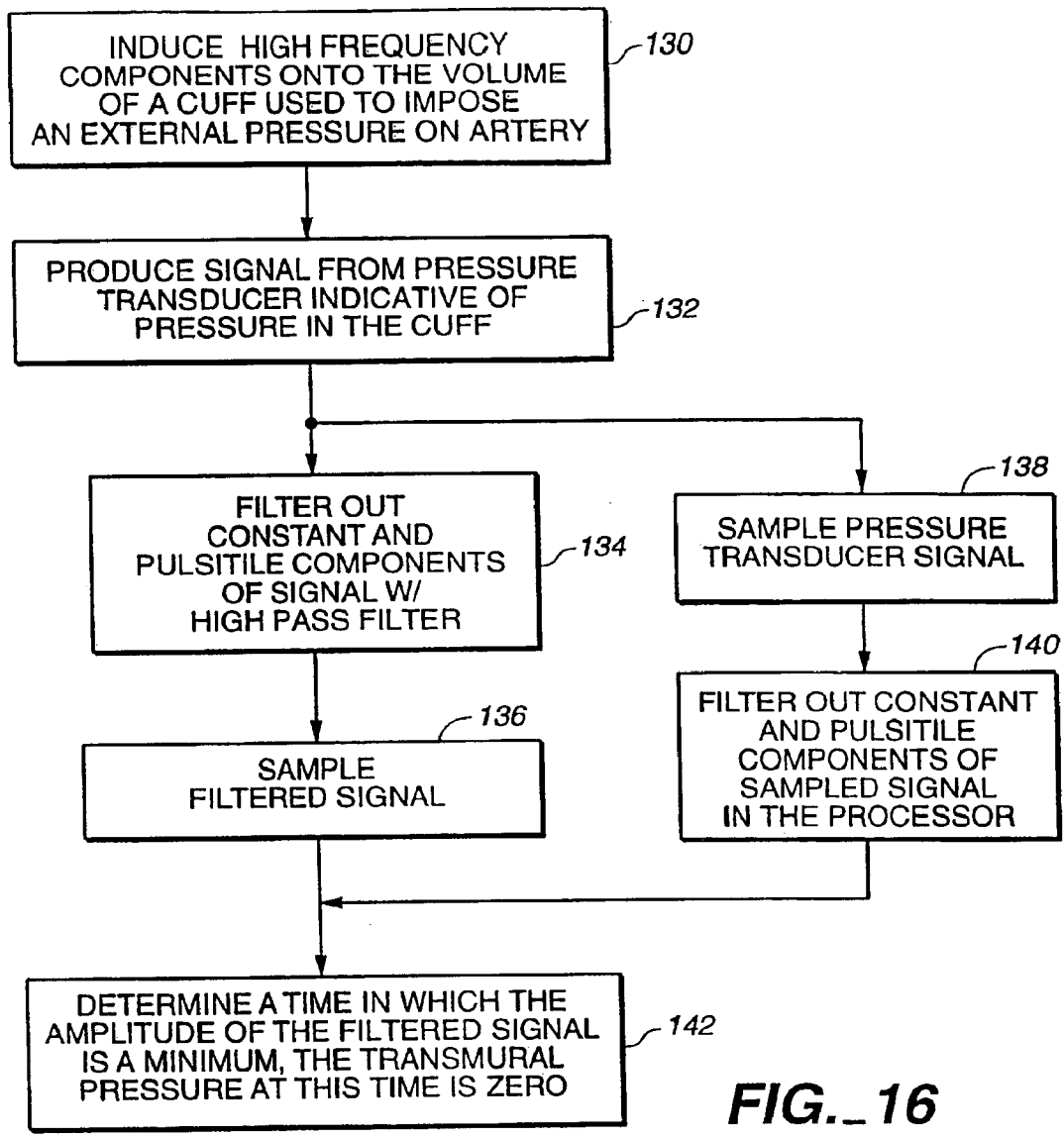
FIG._16
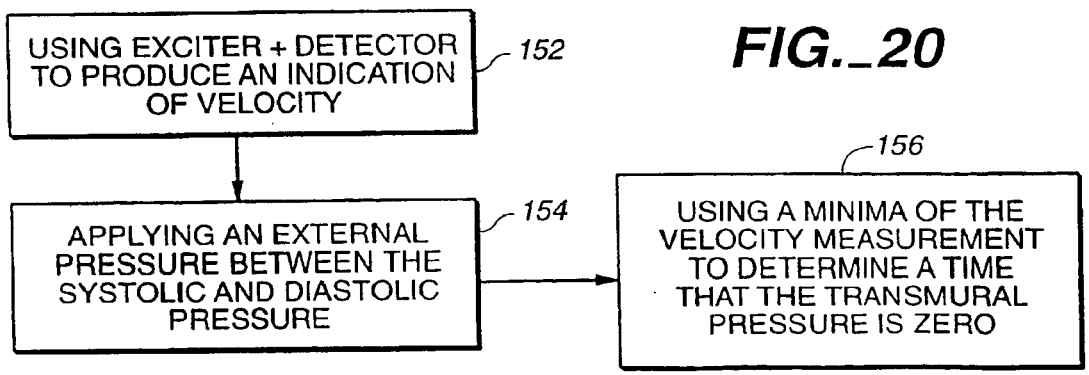
FIG._20

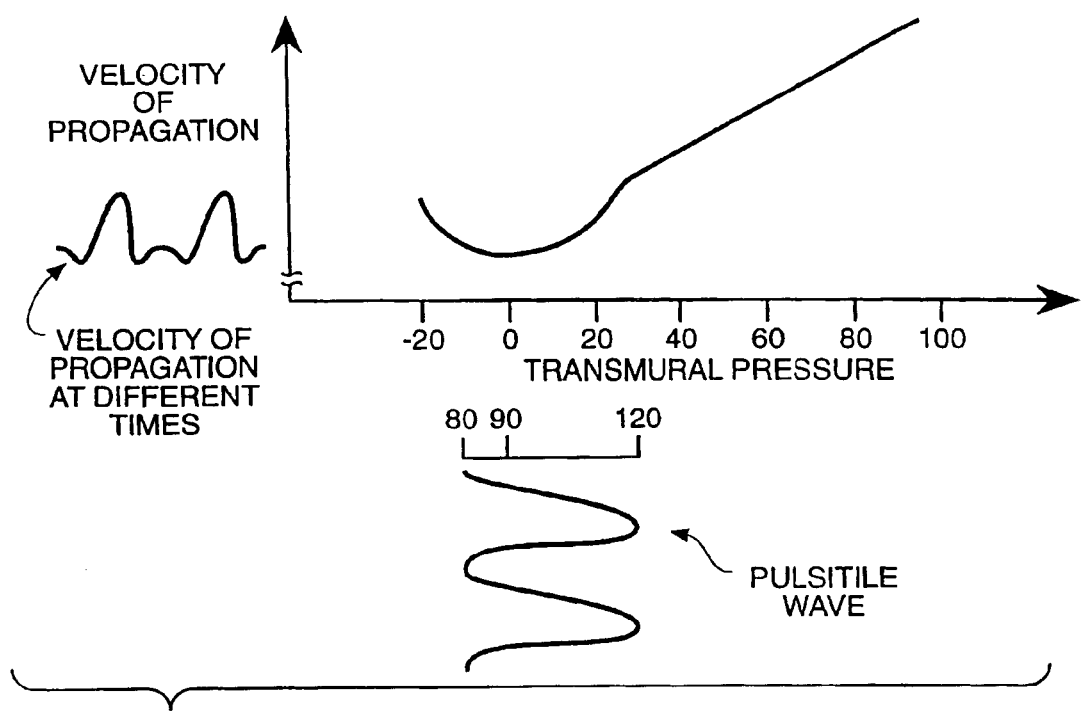
FIG._18
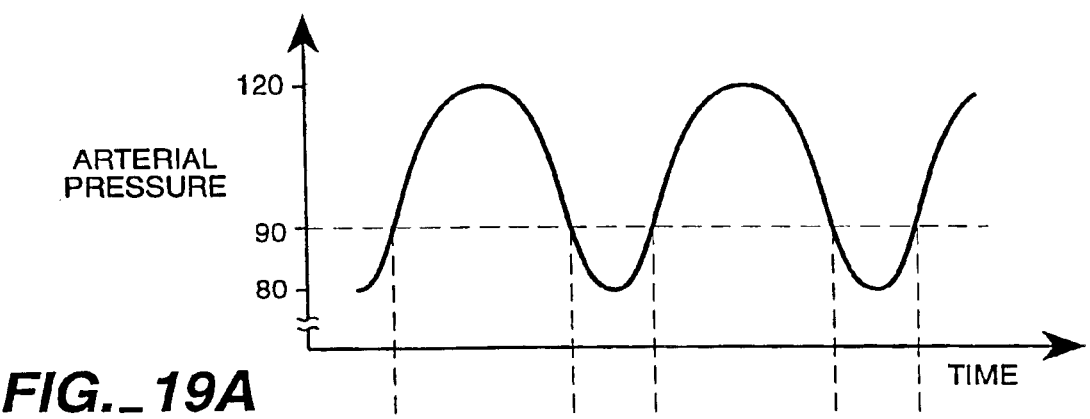
FIG._19A
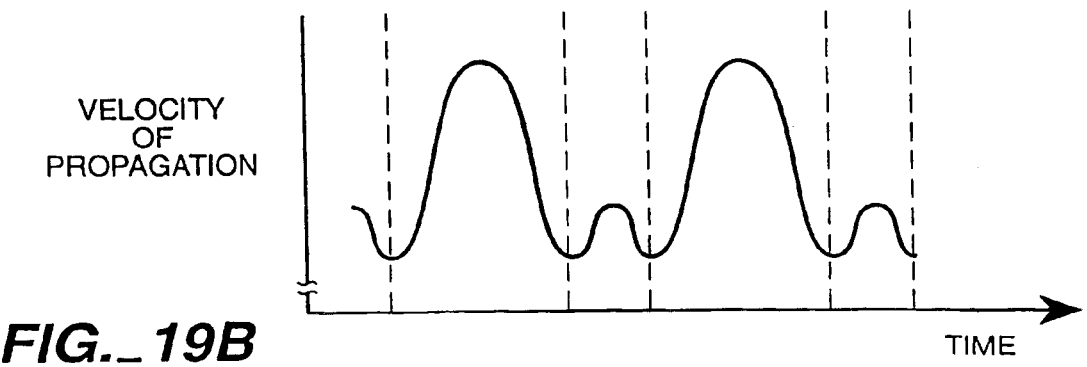
FIG._19B

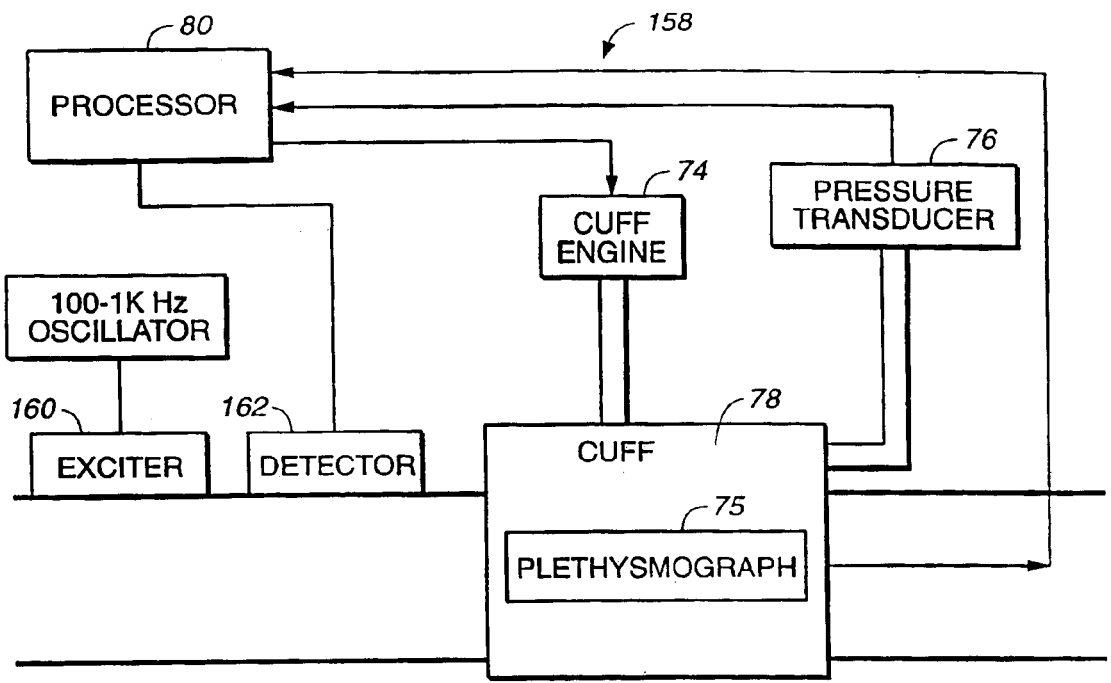
FIG._21
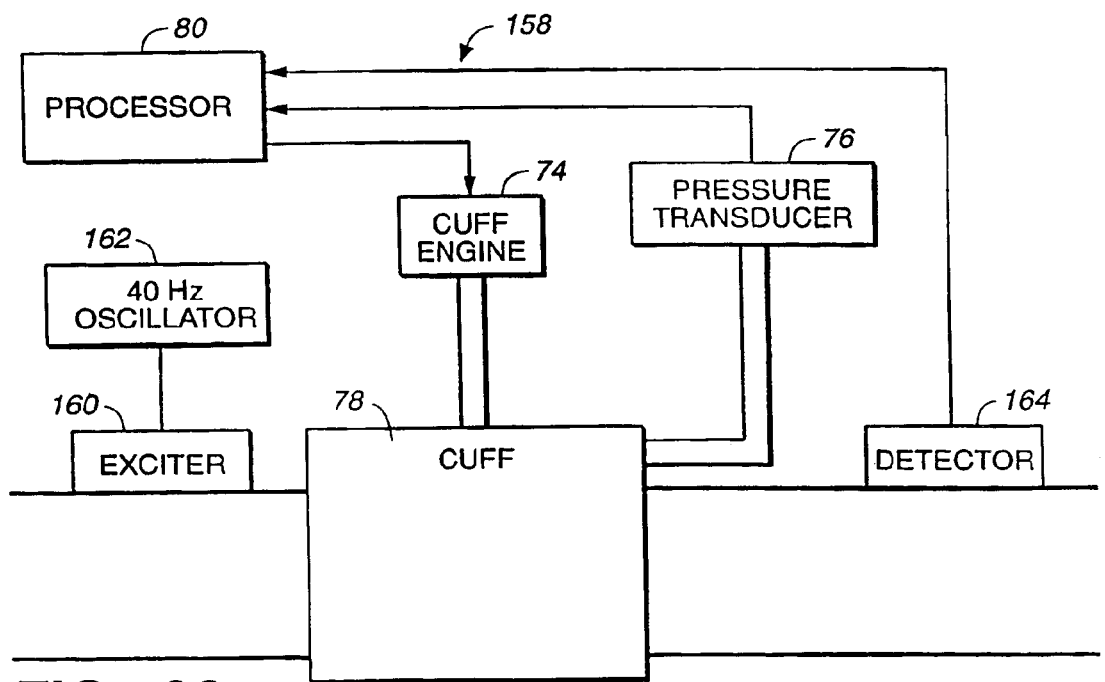
FIG._23

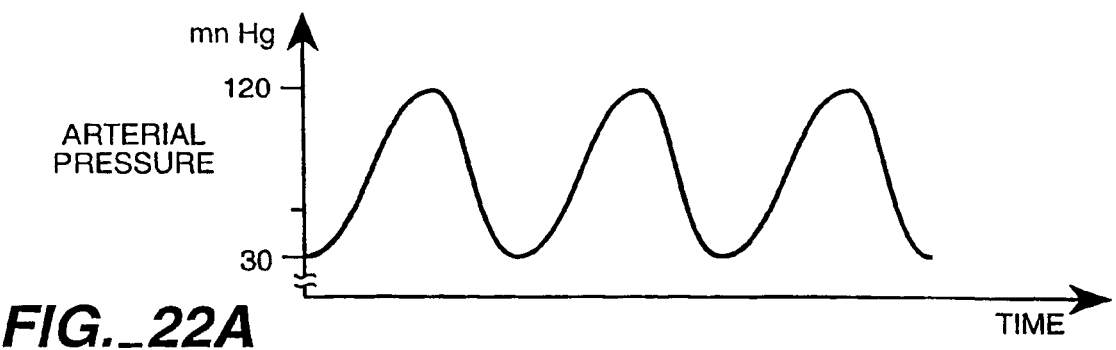
*FIG.\_22A*
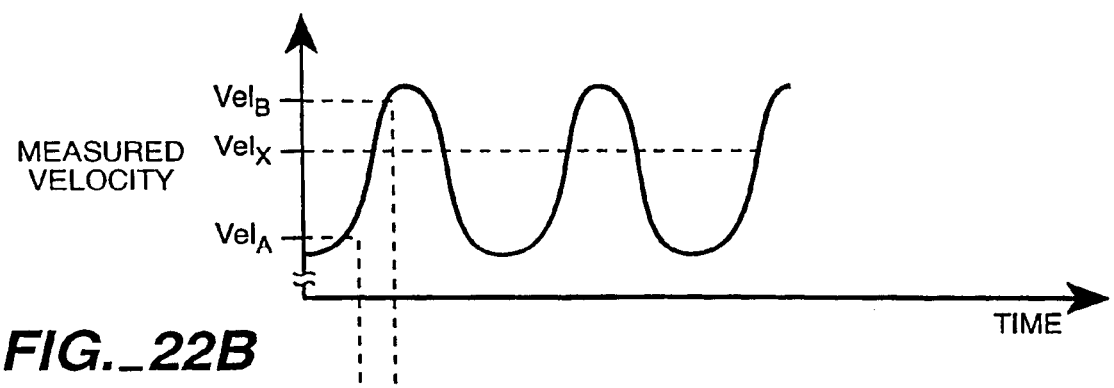
*FIG.\_22B*
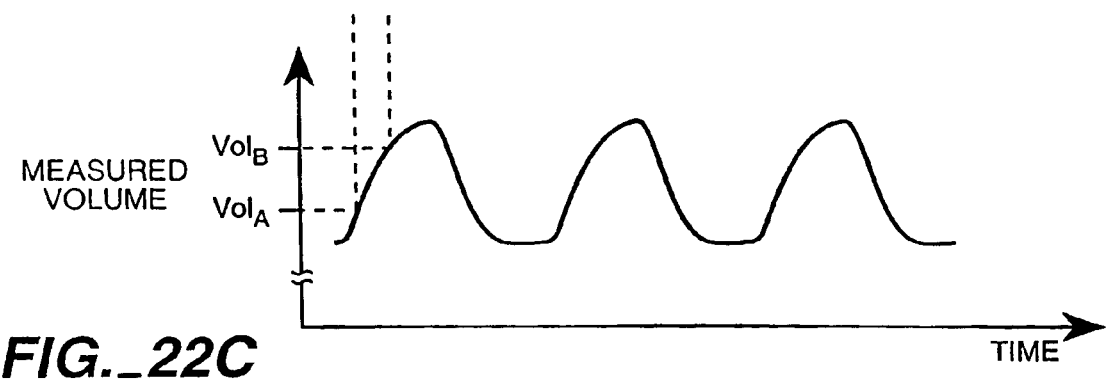
*FIG.\_22C*
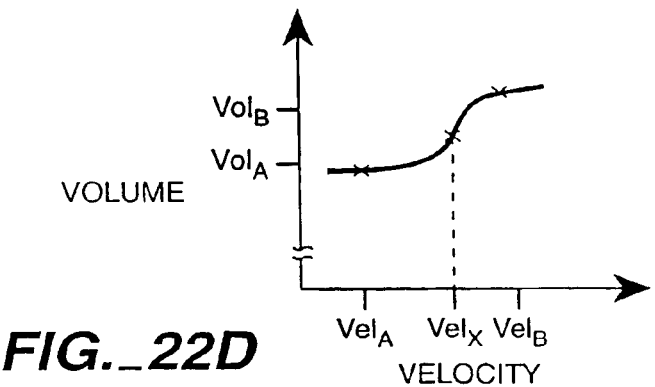
*FIG.\_22D*

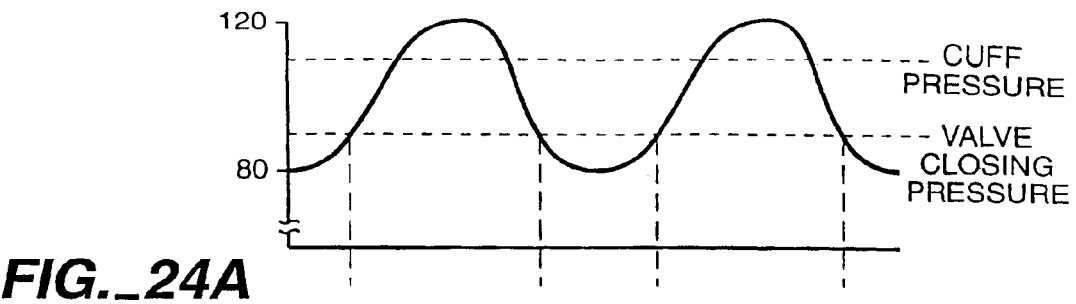
FIG._24A
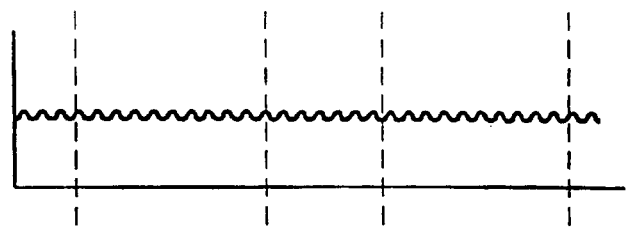
FIG._24B
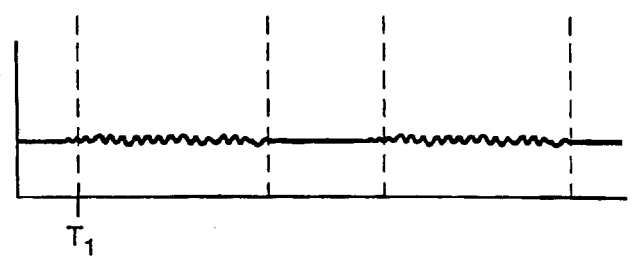
FIG._24C
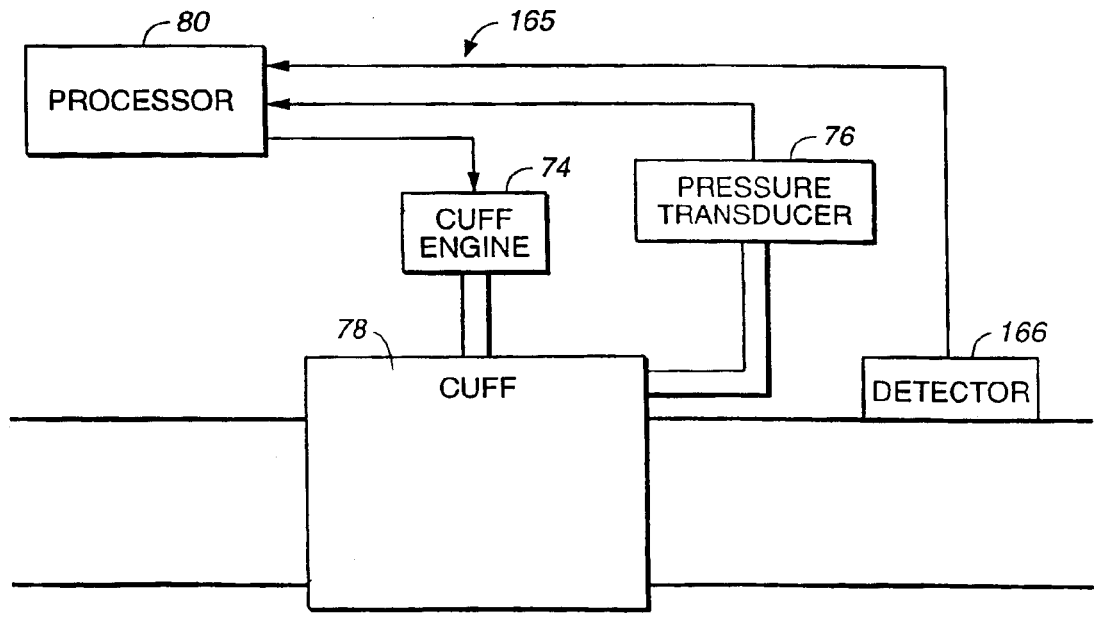
FIG._25

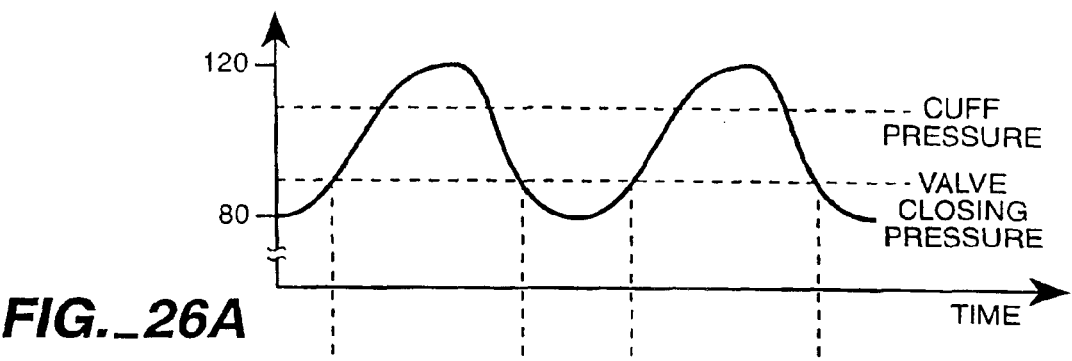
FIG._26A
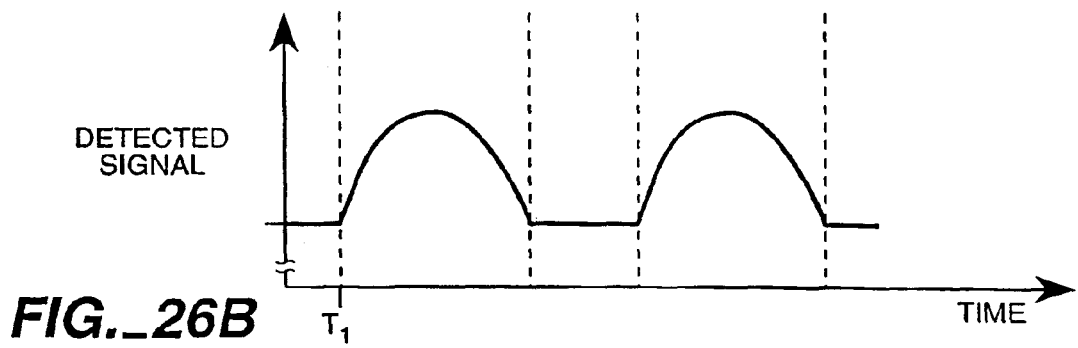
FIG._26B
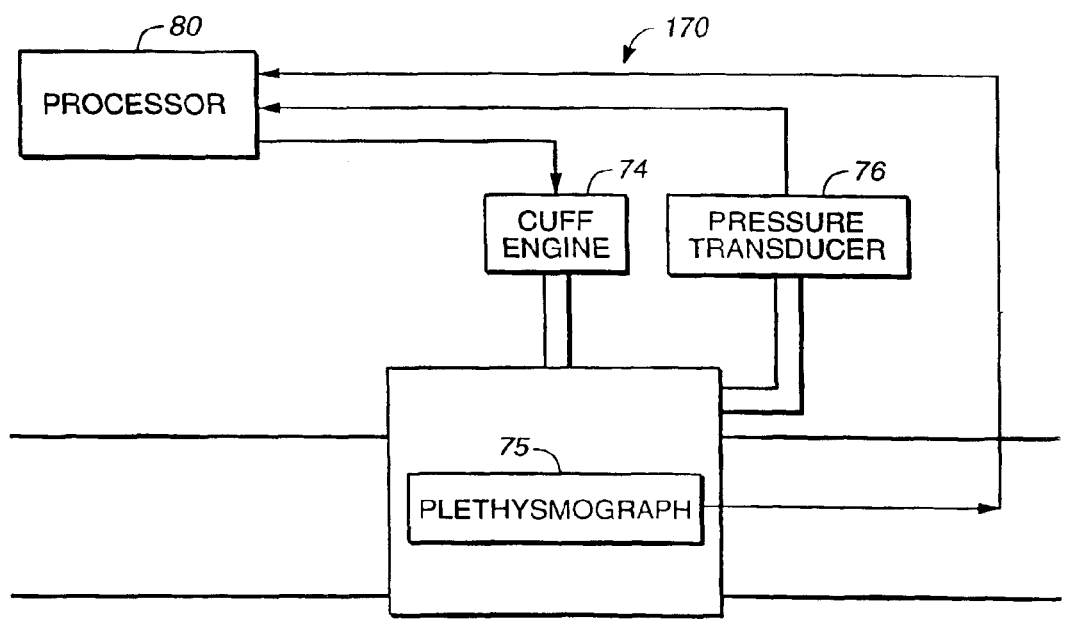
FIG._27

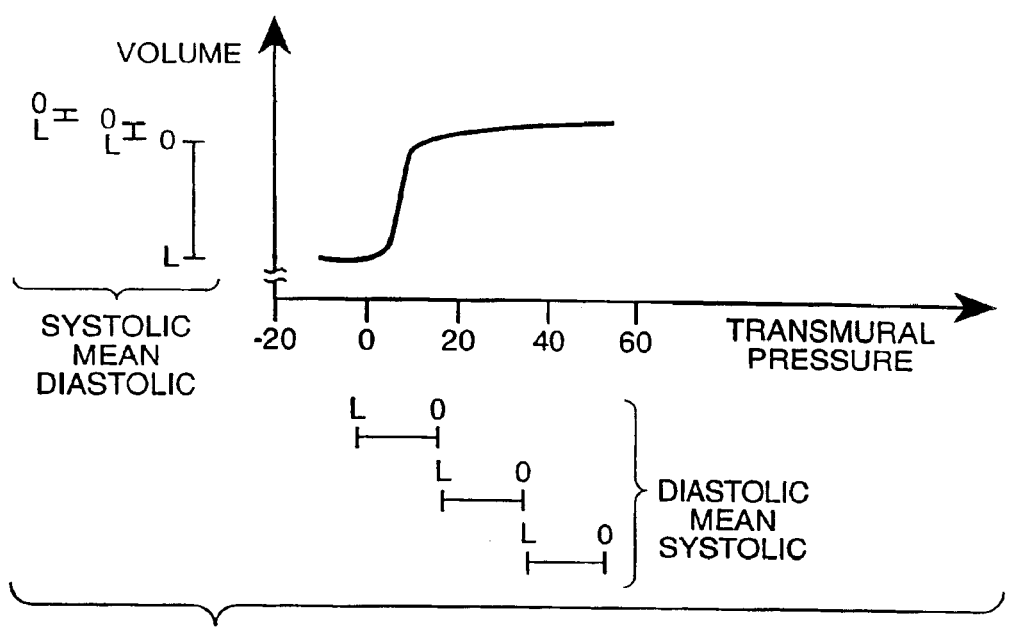
FIG._28
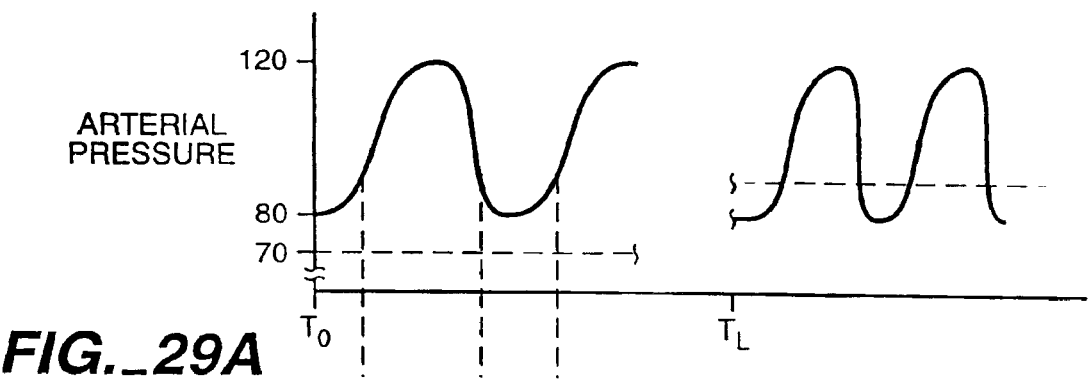
FIG._29A
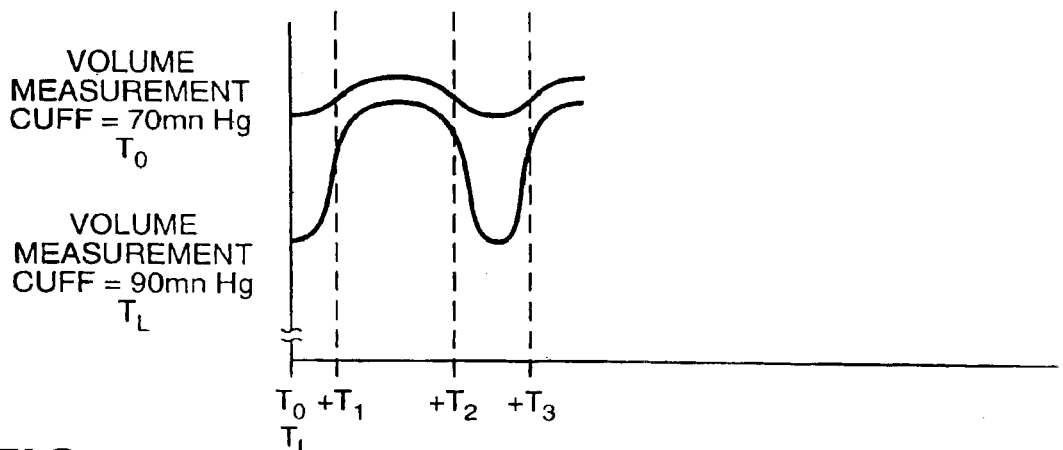
FIG._29B

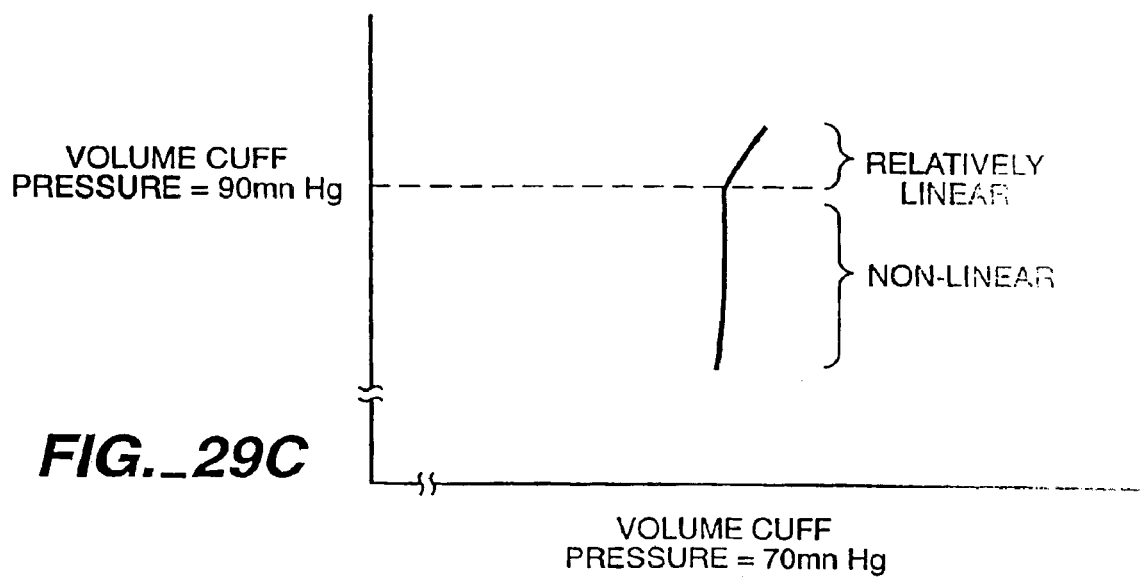

RAPID NON-INVASIVE BLOOD PRESSURE MEASURING DEVICE

RELATED APPLICATIONS

This application is a continuation of U.S. application Ser. No. 09/412,295, filed Oct. 5, 1999 now U.S. Pat. No. 6,632,181, which is a continuation of U.S. application Ser. No. 08/672,218, filed Jun. 26, 1996, now U.S. Pat. No. 6,027,452, all incorporated by reference herein.

BACKGROUND OF THE INVENTION

Field of the Invention

The present invention relates to methods and apparatus for the non-invasive determination of blood pressure.

Direct measurement of blood pressure with a pressure measuring device such as a tonometer is difficult in a clinical setting. A problem with tonometer readings is that although the times of the systolic and diastolic pressures are correct, the pressure readings may have an incorrect scaling or have an offset in the recorded pressure. Tonometer measurements can depend on the position of the tonometer, artery and bone structure behind the artery.

Another prior art system used to determine arterial pressures is an automated oscillometric device called a "Dinamap" (device for indirect non-invasive mean arterial pressure). This device is described in a paper entitled "Arterial Pressure Monitoring: Automated Oscillometric Devices"; M. Ramsey III; *Journal of Clinical Monitoring*; Volume 7, No. 1; January 1991; pp. 56–67. This system uses a cuff to supply an external pressure to an artery. The cuff pressure is stepped in increments from a pressure believed to be above the systolic pressure to a pressure believed to be below the diastolic pressure. An arterial volumetric indication is monitored by the system. For example, a pressure transducer attached to the cuff will give some indication of the volume of the artery, since the pressure in the cuff will be greater when the artery volume is high. When the mean value of the arterial blood pressure is about the same as the external cuff pressure, the amplitude of the variations of the volumetric indication will be the greatest. In this way, an indication of the mean arterial pressure can be obtained. A disadvantage of this prior art system is the considerable time it takes to obtain the arterial pressure information. Many cardiac cycles are needed to obtain the data required to determine a blood pressure.

An alternative system is described in "Vibration Technique for Indirect Measurement of Diastolic Arterial Pressure in Human Fingers"; Shimazu, et al.; *Medical and Biological Engineering in Computing*; March 1999; Volume 27; pp. 130–136. This paper describes a method for obtaining a diastolic pressure which is somewhat similar to the oscillometric technique used with the Dinamap. In the Shimazu, et al. system, a small oscillation is placed on the cuff pressure. A plethysmograph is used to get a volumetric indication of the volume of the artery. The output of the plethysmograph will show a high-frequency component imposed on a pulsatile component. The cuff pressure is ramped or stepped in a manner similar to the Dinamap system. In the cardiac cycle where the cuff pressure is roughly equal to the diastolic pressure, the amplitude of the high-frequency component of the volumetric indication will be greater in the diastolic period of that cycle than at the diastolic period of any other cycle. In this way, the diastolic pressure can be determined. Like the Dinamap system, the Shimazu, et al. system is relatively slow. Many cardiac cycles are required to determine a single blood pressure value.

Another prior art system is described in Penàz U.S. Pat. No. 4,869,261. Penàz describes a vascular unloading system. Vascular unloading systems attempt to cause the external applied pressure to be equal to the arterial blood pressure at all times. These systems use a plethysmograph and a feedback loop in order to adjust the external pressure so that it tracks the arterial pressure. A disadvantage of this system is that, when the external pressure tracks the arterial pressure, the mean applied pressure is relatively high. For this reason, the system described in Penàz may be uncomfortable or painful to use. Additionally, vascular unloading systems tend to produce a pressure signal that is off from the real arterial pressure by a DC offset.

The systems of Palti U.S. Pat. No. 4,660,544 and Sramek U.S. Pat. No. 4,343,314 use very fast ramped external pressures. A disadvantage of these systems is that the required very fast ramped pressures may be impractical to produce. In particular, it may be difficult to use a cuff to apply the external pressures because of the relatively long periods of time required to inflate or deflate a cuff. Additionally, the quick external pressure ramp could be uncomfortable.

Therefore, it is desired to have a method and apparatus for obtaining a blood pressure that can avoid long measurement times or high applied external pressures.

SUMMARY OF THE INVENTION

The present invention is a method and apparatus for quickly determining a blood pressure value at a specific time. An external pressure is supplied to the artery so that the artery experiences a range of transmural pressures. The external pressure is set so that a known event, or marker, will occur during a measurement period. The measurement period is a short period of time that typically can be a cardiac cycle or a few cardiac cycles. The value of the external pressure at the time of the event allows for the calculation of an arterial pressure associated with the time of the event or an earlier or later time in another cardiac cycle.

By allowing a range of transmural pressures within a cardiac cycle, the transmural pressure is not clamped at zero like in the apparatus of the Penàz patent. In one embodiment, the range in the transmural pressure is mainly due to arterial pressure variations.

Examples of events, or markers, that can be detected include a peak in the arterial compliance curve at the transmural pressure about equal to zero or an opening or closing of an artery. Other markers that can be used include a pressure dependant change in attenuation of a propagating pressure wave; frequency dependent effects (i.e. level of attenuation of a propagating wave versus frequency or a compliance versus frequency relationship); changes in a compliance versus attenuation relationship; a change in the viscoelastic properties of the artery or other portion of the body; or a change in the flow of blood through the artery.

Several of the preferred embodiments of the invention use, as a marker, the peak in the compliance of the artery. The peak is, by definition, the transmural pressure (or pressure across the artery wall) where the slope of the pressure-volume relationship of the artery is the steepest. The pressure-volume relationship relates the pressure across the artery wall to the volume in the lumen of the artery. The peak in the compliance indicates that, at that transmural pressure, a given change in transmural pressure will cause a larger change in the volume of the artery than at any other transmural pressure. This peak is thought to occur at a transmural pressure of zero because the artery wall is at the least amount of stress at this pressure.

It is possible that the peak in compliance does not occur at zero transmural pressure, but rather at some transmural pressure close to zero. These slight variations could be caused by a number of factors including: arterial size, presence of disease states, age, gender, etc. The system of the present invention can produce relatively accurate blood pressure values when it assumes the compliance peak occurs at the transmural pressure of zero. If significant variations in the transmural pressure of peak compliance are found to occur, this invention would still function adequately if an appropriate compensating factor were added to the measured pressure.

The time that an event (i.e. transmural pressure approximately zero) occurs is used to produce an indication of the arterial blood pressure at a specific time. For example, if the transmural pressure is equal to zero at time $T_1$, the system knows that the arterial pressure is equal to the cuff pressure at time $T_1$ and/or at a different time with the same position in a subsequent or prior cardiac cycle as $T_1$.

Within as little as single cardiac cycle, all of the data required to determine a blood pressure at a certain time can be obtained. This is much quicker than the many cycles required in the Dinamap and Shimazu systems.

The information of a blood pressure at a certain time can be used to calibrate a blood pressure signal, such as a signal from an arterial tonometer, a pressure wave velocity measurement system, or a vascular unloading device. Alternatively, it may be useful just to have any blood pressure in some situations, especially since the present invention can determine a blood pressure so quickly.

In the present invention, it is not necessary for large changes to be made to the external applied pressure. For this reason, the control of the external pressure is made easier. For example, the external pressure can be applied by a cuff which is inflated with a fluid, such as air or water, to a constant volume. The external pressure would thus be substantially constant.

Some embodiments of the present invention use the fact that there is a peak to the compliance versus pressure curve at a transmural pressure approximately equal to zero. This means that at a transmural pressure approximately equal to zero, small arterial pressure changes can cause large arterial volume changes. These embodiments preferably use an external pressure between the systolic and diastolic pressure. This external pressure can be less than the peak external pressures used in the Dinamap or Penàz systems.

One set of embodiments using this relationship uses an arterial pressure dependent signal and an arterial volume dependent signal to produce a curve of a volume indication versus a pressure indication. These embodiments are called pressure/volume embodiments. The maximum rate of change of this curve will be at a transmural pressure approximately equal to zero. Alternately, the curve can be fitted to a polynomial equation. A derivative of the polynomial equation can be obtained to get an equation that is related to the compliance. A maximum of this compliance equation would be at a transmural pressure approximately equal to zero. This means that, when the arterial pressure dependent signal has a value such that the compliance related value has a maximum, the arterial pressure is approximately equal to the externally-applied pressure. The time at which the transmural pressure is approximately equal to zero is obtainable, since the system knows the value of the pressure-dependent signal at different times.

These embodiments can also work if there is a nonlinear dependence of the pressure-dependent signal or volume-dependent signal to the actual arterial pressure or arterial volume. This is because, in the present embodiment, only a maxima or maximum rate of change of a curve is required to be determined.

Examples of arterial pressure-dependent signals that can be used include a tonometer or other pressure sensors, or a system which measures the velocity of wave propagation in the artery. The pressure wave velocity is monotonically-related to the arterial pressure. Alternately, a pressure signal from a vascular unloading device could be used as a pressure dependent signal.

The volume-dependent signal can be obtained from a plethysmograph. Alternatively, the volume-dependent signal can be obtained from a pressure transducer connected to the cuff used to provide the external pressure. Increases in the arterial volume will cause the pressure within the cuff to increase. Decreases in arterial volume will cause the pressure in the cuff to decrease.

Another set of embodiments of the present invention use an exciter to put a high frequency pressure signal onto the blood pressure or the external pressure. This set of systems will then look at a volume-related signal to obtain an indication of the time that the transmural pressure is equal to zero. The input signal is at a higher frequency than the pulsatile components. The pulsatile components generally have relatively low frequencies. The volume-related signal can be filtered so that the high frequency output of the volume-related signal is obtained. The greatest amplitude of this high frequency signal will be at a point of the cycle in which the transmural pressure is equal to zero. The time within a cardiac cycle that the transmural pressure is equal to zero can be obtained with a precision that depends on the frequency of the exciter signal. The volume-related signal such as a plethysmograph can be filtered with a high-pass filter to get the high frequency component.

Another set of embodiments use a system identification approach. For example, a constant amplitude volume oscillation to the volume of the external pressure cuff can cause a volume change of the artery. A pressure indicative signal can be filtered to obtain the high-frequency component. The minimum amplitude of this high frequency component of the pressure changes would occur at the time of maximum compliance. Other alternative embodiments are also possible.

Yet another set of embodiments concern the arterial closing or opening. The arterial opening and closing will usually occur at a certain transmural pressure. A high frequency pressure signal can be sent towards an artery that has an applied external pressure. When the artery closes, the signal will be blocked and/or reflected. This means that the external pressure can be set such that within a cardiac cycle, a time can be obtained that the artery opens or closes.

Another embodiment uses a critical value associated with viscosity. Pressure wave velocity measuring system can be used to produce an indication of the attenuation of the pressure signal that is related to the viscosity. A critical value in the viscosity can be used such that by looking at the attenuation of the pressure signal an arterial pressure can be obtained.

In another embodiment, it an event can be identified in a pressure wave that propagates through tissue other than the artery, such as bones, skin, muscle, tendon, etc. For this system, the transfer function is calculated for the portion of the detected pressure wave signal that travels via paths other than the artery. The marker can be obtained by the change in the relationship between phase, amplitude and frequency, of the propagated pressure. Another embodiment of the present invention uses the existence of harmonics to determine a certain specific time at which the arterial pressure has a certain value. Non-linear transfer functions, such as the arterial-volume/transmural-pressure curve, can cause harmonics to be produced. This means that a detector using a band-pass filter set at a frequency which is a multiple of an input exciter frequency will produce a signal that can give information about a critical transmural pressure, such as the transmural pressure equal to zero.

Additionally, blood flow can be manipulated to produce a marker at a particular transmural pressure. For example, the peak flow velocity in a section of artery increases if the compliance of a distal segment of the artery were decreased. The compliance of a distal section of the artery can be changed by applying an external pressure, and would have a maximum at a transmural pressure of zero. Other changes are measured if the flow meter is placed immediately distal to the segment of the artery where the transmural pressure was manipulated. The measurements of the blood flow can be done with a Doppler flow meter.

BRIEF DESCRIPTION OF THE DRAWINGS

The above and other features and aspects of the present invention will become more apparent upon reading the following detailed description in conjunction with the accompanying drawings, in which:

FIG. 1 is a diagram of the apparatus of the present invention.

FIG. 2 is a flow chart illustrating the method of the present invention.

FIG. 3 is a diagram illustrating the use of the present invention in a simultaneous measurement system.

FIG. 4 is a diagram illustrating the method of the present invention used in a sequential measurement system.

FIG. 5 is a diagram illustrating an embodiment of the present invention using a tonometer to produce a pressure-indicative signal and a plethysmograph to produce a volume-indicative signal.

FIGS. 6A–D are graphs illustrating the operation of the embodiment of the present invention shown in FIG. 5.

FIG. 7 is a flow chart illustrating the operation of the processor used in the embodiment of FIG. 5.

FIG. 8 is a diagram illustrating an embodiment of the present invention using an externally-applied signal and obtaining an arterial volume-related signal with the use of a plethysmograph.

FIG. 9 is a diagram of an apparatus of the present invention using an exciter and a pressure transducer attached to a cuff to obtain an arterial volume indicative signal.

FIG. 10 is a graph illustrating the relationship between cross-sectional area or volume and the transmural pressure.

FIG. 11A–C are graphs illustrating the operation of the embodiments of FIGS. 8 or 9.

FIG. 12 is a flow chart illustrating the operation of the processor of FIG. 8.

FIG. 13 is a diagram illustrating an embodiment of the present invention using a constant volume high-frequency input to the cuff.

FIG. 14 is a graph illustrating the dependence of cross-sectional area or volume with respect to the transmural pressure.

FIGS. 15A–D are graphs illustrating the operation of the apparatus of FIG. 13.

FIG. 16 is a flow chart illustrating the operation of a processor used in FIG. 13.

FIG. 17 is a diagram illustrating an embodiment of the present invention in which a velocity-dependent measurement is made with the exciter and detector for the velocity determining operation being placed underneath an external pressure-applying cuff.

FIG. 18 is an illustration of the velocity of propagation of a pressure wave versus the transmural pressure in the artery.

FIGS. 19A–B are graphs illustrating the embodiment of FIG. 17.

FIG. 20 is a flow chart illustrating the operation of the processor of FIG. 17.

FIG. 21 is a diagram illustrating an embodiment of the present invention in which a pressure wave velocity is determined to obtain a pressure-related signal outside of the external pressure-applying cuff and a volume-related signal is obtained by the plethysmograph inside of the external pressure-applying cuff.

FIGS. 22A–D illustrate the operation of the embodiment of FIG. 21.

FIG. 23 is a diagram illustrating an embodiment of the present invention that operates to determine the time that an artery is opened or closed.

FIGS. 24A–C are graphs illustrating the operation of the embodiment of FIG. 23.

FIG. 25 is a diagram illustrating an alternate embodiment of the present invention that operates to determine the time that an artery is opened or closed.

FIGS. 26A–B are graphs illustrating the operation of the embodiment of FIG. 25.

FIG. 27 is a diagram of an apparatus of the present invention using a plethysmograph to obtain an arterial volume-indicative signal in two different cardiac cycles with two different external pressures.

FIG. 28 is a graph illustrating the relationship between volume and the transmural pressure.

FIGS. 29A–C are graphs illustrating the operation of the embodiment of FIG. 27.

DETAILED DESCRIPTION OF THE PREFERRED EMBODIMENT

FIG. 1 is a diagram of an apparatus 30 of the present invention. This embodiment uses an external pressure-applying device 32, which applies an external pressure onto an artery 34a in a part of the body 34. Also shown is a bone 34b behind the artery 34a. The external pressure-applying device can be, for example, a cuff, such as a Duracuff available from Critikon. Any other device providing a controlled external pressure could also be used. A detector 36 can be used to detect a physiological signal. In some of the embodiments described below, detector 36 will be used to obtain an arterial pressure-indicative signal or an arterial volume-indicative signal.

Optionally, an exciter 38 can be used to produce an induced high-frequency perturbation on the artery that can be detected by the detector 36. The output of the detector 36 may be filtered. The detector 36 can be positioned at positions A, B or C shown in the figure.

A processor 40 is used to analyze the data obtained by the detector or detectors. The processor can be, for example, a computer with appropriate hardware to capture analog signals, such as an IBM PC with an analog-to-digital converter. Alternatively, a dedicated processor could be used.

FIG. 2 is a flow chart illustrating the method of the present invention. In step 42, an external pressure is applied to an artery, the external pressure being such that the artery experiences a range of transmural pressures within a cardiac cycle. Allowing a range of transmural pressures within a cardiac cycle can help avoid some of the difficulties of the system of the Penàz patent. In some embodiments, the range of transmural pressures is produced by applying a substantially constant external pressure to a section of the artery.

Steps 44–46 are preferably done by the processor 40. In step 44, an event occurring at a transmural pressure in said range of transmural pressures is identified, the event being associated with a first time. The event can be, for example, a peak in the arterial compliance curve at the transmural pressure equal to zero. The event could also the closing or opening of an artery. In some embodiments, the time is determined without requiring data from outside a measurement period.

As will be described below with respect to the specific embodiments, this step can be done in a variety of ways. For example, data from a pressure-indicative signal and a volume-indicative signal can be used to produce a curve which indicates a time at which the transmural pressure is equal to zero, or an exciter signal component can be used to indicate a time within a cardiac cycle at which the transmural pressure is zero.

In step 46, the arterial pressure is at a specific time determined. This specific time can be the time of the event identified, or it can be another time. For example, the time of the event can be measured in terms of a percentage of the cardiac cycle time from a diastolic pressure. Thus, at another time outside of the measurement period, it can be determined that at a specific time which is the same percentage of a cardiac cycle from the diastolic pressure, the arterial pressure is the determined value.

FIGS. 3 and 4 are flow charts illustrating different ways of using an arterial pressure indication produced by the present invention to calibrate a pressure-tracking signal. In the simultaneous measurement system of FIG. 3, at the same time an external pressure is applied in step 52, and the marker event measured in step 54, a pressure-tracking signal is determined in step 56. For example, the pressure-tracking signal can be a signal from a tonometer; a pressure wave velocity determination where the pressure wave velocity is linearly related to the pressure; or the signal from a vascular unloading device. In step 58, the pressure marker, that is, the indication of a blood pressure at a time, can be used to calibrate the pressure-tracking signal. In the sequential measurement system of FIG. 4, the pressure-tracking signal is recorded in step 60, an external pressure is applied in step 62, a measured event determined in step 64. Next a pressure-tracking signal is recorded again in step 66, and in step 68, the pressure marker is used to calibrate the pressure-tracking signal. Sequential measurement, as described in FIG. 4, would be advantageous for systems in which the application of the external pressure for determining the marker event would prevent an accurate pressure tracking signal.

The pressure signal to be calibrated can be from an arterial tonometer, a pressure wave velocity measurement system or a vascular unloading system.

FIG. 5 is a diagram of an apparatus 70 using a tonometer 72 to produce a pressure-indicative signal and a plethysmograph 75 to produce an arterial volume-indicative signal. Although the tonometer 72 gives an arterial pressure indication, tonometers by themselves are typically not sufficiently accurate. The tonometer readings depend upon their placement with respect to the artery and the underlying bone. For that reason, the readings of the tonometer cannot accurately be used to produce an actual arterial pressure. A cuff engine 74 can be used to inflate a cuff to a desired pressure, as indicated by the pressure transducer 76. The cuff pressure is inflated to the desired external pressure.

In a preferred embodiment, the cuff 78 is inflated to produce an external pressure such that the desired event will occur at least once during each cycle. If the desired event to be identified is the transmural pressure equal to zero, the external pressure is maintained at a value between the systolic and diastolic pressure. Such an external pressure will be relatively easy to estimate. Additionally, the externally applied pressure can be modified over different cardiac cycles to find a pressure between the diastolic and the systolic.

The plethysmograph can be a photo-plethysmograph such as a device that uses an light emitting diode (LED) or other light source to shine light through an artery to a detector. A change in the artery volume changes the transmission of the light through the artery, producing an arterial volume indicative signal. The plethysmograph could also be an impedance plethysmograph. An impedance plethysmograph sends an electrical signal through an artery so that the detected signal provides an indication of the arterial volume. Additionally, a piezoelectric plethysmograph, pressure or displacement transducers or strain gages can be used.

FIGS. 6A–D illustrate the operation of the apparatus 70 of FIG. 5. FIG. 6A is a pressure-indicative signal from a tonometer. FIG. 6B illustrates a volume-indicative signal from a plethysmograph. These signals can be used to produce a curve of volume versus pressure shown in FIG. 6C. The processor can associate a measured pressure with a measured volume occurring at the same time. For example, the measured pressure $P_a$ occurs at the same time $T_a$ as the measured volume $V_a$, and the measured pressure $P_b$ occurs at the same time $T_b$ as the measured $V_b$. From such measured pressure/measured volume pairs, a graph such as the graph of FIG. 6C can be produced. In this graph, the greatest rate of change of the measured volume versus measured pressure will occur at a pressure $P_x$ which is associated with the time $T_x$. It is known that the greatest rate of change of an arterial volume versus arterial pressure occurs at the transmural pressure equal to zero. Thus, the transmural pressure would be equal to zero at time $T_x$ and the arterial pressure is equal to the applied external pressure at this time.

Alternately, the graph of FIG. 6A can be fitted to a polynomial equation and a derivative equation produced. FIG. 6D is a graph of compliance versus measured pressure obtained with the derivative equation. At the maximum of the compliance equation, at a pressure $P_x$ (associated with time $T_x$), the transmural pressure is equal to zero.

Thus, the present invention allows for an arterial pressure indication to be produced from data obtained over as little as a single cardiac cycle. This arterial pressure indication is not necessarily the systolic and diastolic pressure. This arterial pressure indication can be used to calibrate a pressure-indicative signal.

Looking again at FIG. 6A, assuming that the tonometer is off from the real pressure value by a scale constant $C_1$, and an offset constant $C_2$. The equation real arterial pressure=$C_1$ measured pressure+$C_2$ will apply. The tonometer can be calibrated with two determinations of the real pressure obtained at different cuff pressures. For example, assuming at time $T_x$, the real pressure $RP_x$ is equal to the cuff pressure, $CP_x$, and the measured pressure is $MP_x$; and at time $T_y$, the real pressure $RP_y$ is equal to the cuff pressure, $CP_y$, and the measured pressure is $MP_y$, then $$C_1 = \frac{CP_x - CP_y}{MP_x - MP_y} \quad \text{and}$$

$$C_2 = \frac{MP_x CP_y - MP_y CP_x}{MP_x - MP_y}$$

Alternatively, the processor could use other well-known algorithms to scale the arterial pressure indicative signal.

If the vascular unloading system is used, the method of the present invention can be used to provide the correct DC offset.

A system that operates in a similar manner to that described with respect to FIGS. 5 and 6 is described below with respect to FIGS. 21 and 22. The system of FIGS. 21 and 22 uses a pressure wave velocity signal to give an indication of the arterial pressure.

FIG. 7 is a flow chart illustrating the operation of the processor 80 of FIG. 5. In step 90, the tonometer, plethysmograph and time are sampled. The time can be a time derived from a clock signal. In step 92, ordered pairs of the sampled volume and sampled pressure can be formed into a graph of measured volume versus measured pressure as shown in FIG. 6C. In step 94, the graph is fitted with a polynomial equation that gives volume in terms of pressure. Such a polynomial fitting to a graph is a well-known data-processing technique. In step 95, a derivative of the polynomial equation can be produced. The production of a derivative equation from a polynomial equation is well known. The derivative equation will give compliance indication with respect to a measured pressure. In step 96, the maximum of the compliance is used to give the measured pressure at which the transmural pressure is zero. This means that the arterial blood pressure is equal to the external applied pressure. A time associated with the measured pressure at the maximum is attained. In the optional step 98, the time and the pressure reading is used to calibrate a tonometer output. This can be done by producing a constant by which all the tonometer readings are multiplied.

FIG. 8 illustrates an exciter system 100 using the exciter 102 to produce an induced high-frequency signal which is detected by plethysmograph 104. In one embodiment, the plethysmograph produces a volumetric indication which is filtered by the high-pass filter 106 to isolate the high-frequency component induced by the exciter 102. This high-frequency indication is sent to the processor 80. In a preferred embodiment, a 40 Hertz oscillator 108 is used to produce an electrical signal to control the exciter 102 so that a 40 Hertz pressure wave signal is imposed on the blood pressure. A 25 Hertz high-pass filter 106 will pass the 40 Hz frequency components from the exciter, but will filter out many of the lower-frequency pulsatile components. The exciter can be a small speaker having an oscillating electrical input. In one embodiment, the exciter and detector can be at the same location.

FIG. 9 is a diagram of an apparatus 110 that uses the pressure transducer to produce the volume-indicative signal. This volume-indicative signal is filtered in the high-pass filter 106 and sent to processor 80.

FIG. 10 is a graph of the cross-sectional area versus the transmural pressure. If a constant high-frequency pressure component is applied at different baseline pressures, the high-frequency output in a volume-indicative signal will be the greatest at around zero transmural pressure, as shown in FIG. 10.

FIGS. 11A–C are graphs illustrating the operation of the apparatus of FIGS. 8 and 9. FIG. 11A is a graph of the arterial blood pressure with an imposed high-frequency component. As with all the arterial pressure graphs in the present invention, this graph is simplified for the purpose of clarity. FIG. 11B is a graph illustrating a filtered high-frequency component of the cross-sectional area obtained with a filtered plethysmograph signal or a filtered pressure transducer signal. FIG. 11C illustrates the amplitude of the high-frequency component of the volume or cross-sectional area indicative signal. Note that the amplitude is greatest at the point that the blood pressure equals the cuff pressure (transmural pressure approximately zero).

Note that by changing the cuff pressure, the diastolic or systolic pressure can be found. When the cuff pressure is reduced to the diastolic pressure, peak A will merge with peak B. When the cuff pressure is increased to the systolic pressure, peak B will merge with peak C.

Additionally, if the cuff pressure is greater than the systolic or less than the diastolic, the amplitude of the high-frequency component will be smaller and more constant without the peaks associated with a transmural pressure of around zero. Thus, the system of the present invention can use multiple iterations to ensure that the cuff pressure is between the systolic and diastolic.

FIG. 12 is a flow chart illustrating the operation of the processor 80 of FIG. 8. In step 112, the high-frequency component is induced onto a blood pressure signal with an exciter. In step 114, a signal indicative of the cross-sectional area is produced with the plethysmograph. This signal can be filtered in step 116 with a high-pass filter which filters out pulsatile frequency components. In step 118, the filtered signal can be sampled with an Analog-to-Digital converter, and then sent into the processor. Alternately, the plethysmograph signal itself can be sampled in step 120, and this sampled signal filtered within the processor to remove the pulsatile components in a step 122. In step 124, a time that the amplitude of the filter signal is a maximum is determined. The transmural pressure at this time is zero. Thus, the arterial blood pressure at this time is equal to the external pressure.

Another set of embodiments use a system identification approach. Typically, in system identification, a system is perturbed and a response is measured. For example, the compliance can be directly probed by perturbing the artery with either a pressure or volume perturbation and recording the resulting volume or pressure response.

One way to do this is to provide a constant amplitude high-frequency volume perturbation and record the resulting pressure response. An example of such an approach is described below with respect to FIG. 13. FIG. 13 is a diagram illustrating an apparatus 126 which uses a device 128 to produce a small constant amplitude change in the cuff volume. The volume of the cuff vibrates a small amount due to the induced volume change by the device 128. In a preferred embodiment, a standard oscillometric cuff 78 is modified to provide a constant volume perturbation. This modification consists of device 128 that preferably comprises a piezoelectric speaker (not shown) attached to the cuff such that the diaphragm of the speaker forms part of the outside wall of the cuff. Movement of the speaker diaphragm changes the volume of the cuff. The displacement of the cuff 78 is sensed by an accelerometer (not shown) that is used in a feedback circuit to control the displacement of the diaphragm and ensure that it is constant even when the pressure inside the cuff changes. The device 128 also could be a piston (not shown) attached to a rotating disk (not shown) to produce a constant volume change in the cuff 78.

The cuff 78 is inflated by a cuff engine 74 that can inflate the cuff to a predetermined pressure and then close a valve (not shown) to seal the cuff volume. The cuff engine 74 and valve are connected to the processor 80 by a serial cable. This allows the processor 80 to control the inflation of the cuff 78 and the closing of the valve.

The pressure inside the cuff 78 is sensed by a pressure transducer 76, such as Micro Switch Model No. 142PC15G, mounted inside the cuff. A processor 80 that is capable of capturing analog waveforms and performing mathematical computations is used to record and process the signals. This processor 80 could be a general purpose computer that has additional analog-to-digital hardware, or it could be a custom processor.

The device works as follows. The cuff 78 is wrapped around the patient's arm and secured with a Velcro T™ strap. The processor 80 sends a signal to the cuff engine 74 to inflate the cuff 78 to some value between the systolic and diastolic pressure. The desired DC cuff pressure could be determined by either a previous blood pressure measurement, from the calibrated prediction of propagation velocity, tonometer or vascular unloading system, or it could be determined iteratively through successive attempts at measuring the pressure with the present invention. The piezoelectric speaker is activated at this point to provide the constant amplitude volume perturbation. This perturbation is typically a sinusoidal oscillation at about 25 Hertz, but could be a variety of waveforms. The amplitude of the recorded pressure signal will depend upon the compliance of the cuff. This compliance is largely determined by the compliance of the arm, since the arm is supporting one side of the cuff. The arm compliance is partially determined by the compliance of the artery. Thus, the pressure inside the cuff is partially determined by the compliance of the artery. When the artery compliance is a minimum, the pressure oscillation will be minimum. The processor 80 records the 25 Hertz pressure oscillations in the cuff for at least one cardiac cycle. The processor 80 then calculates the amplitude of this pressure oscillation as a function of time. This can be done in a variety of ways, the simplest of which is to calculate the peak-to-peak amplitude for each cycle (this is the difference between the minimum and maximum values of the pressure signal over a four-millisecond period). The time at which the pressure oscillation is a minimum indicates the time when the compliance is maximum and thus the time when the DC cuff pressure is approximately equal to the applied pressure.

It should be noted that this system identification approach to probing compliance can be accomplished in a number of ways. In this embodiment, the volume was oscillated and the resulting pressure was recorded. It is, of course, possible to perturb or oscillate the pressure, and measure the arterial volume oscillation response to find the peak in compliance. In addition, it is usually not necessary to control the perturbation signal, as illustrated in this embodiment. It is usually sufficient to measure the perturbation amplitude and track the ratio of the output response to the input response. It also should be noted that the relationship between the input and output need not be described by a simple ratio of amplitudes, but the relative phases can be accounted for by more complicated mathematical descriptions such as complex transfer functions, auto-regressive moving average (ARMA) models or other mathematical descriptions.

FIG. 14 is an illustration of the cross-sectional area versus transmural pressure. Notice that a constant amplitude high-frequency component of a cross-sectional area signal input produces the smallest high-frequency component pressure signal output when the baseline transmural pressure is at zero. This fact is used in the operation of the embodiment of FIG. 13.

FIGS. 15A–D illustrate the operation of the embodiment of FIG. 13. FIG. 15A shows a high-frequency volume signal which illustrates the change in the volume of a cuff. FIG. 15B illustrates the blood pressure. FIG. 15C illustrates a cuff pressure showing the imposed high-frequency component. FIG. 15D is a filtered high-frequency pressure transducer signal. This figure illustrates that the amplitude of this signal is lowest at the points at which the blood pressure is equal to the transmural pressure.

FIG. 16 illustrates a method of operation of the apparatus shown in FIG. 13. In step 130, high-frequency components are induced in the volume of the cuff used to produce the external pressure onto the artery. In step 132, a signal is produced from the pressure transducer indicative of the pressure in the cuff. In step 134, this signal is filtered to take out the constant and pulsatile components of a signal with a high-pass filter. In step 136, this filtered signal is sampled by an Analog-to-Digital converter (not shown) and sent to the processor. Alternatively, the pressure transducer signal can be sampled in step 138 and then sent to the processor. The processor can filter out the constant and pulsatile components of the sample signal in step 140. In step 142, the processor determines a time at which the amplitude of the filtered signal is at a minimum. At this time, the transmural pressure is zero.

Those skilled in the art will realize that other system identification embodiments can be used with the present invention. For example, although the above system measures a pressure response to a volume perturbation, it is also possible to have a pressure perturbation and measure a volume response. Additionally the perturbation need not be controlled or held constant. Measuring the perturbation is sufficient in most cases.

FIGS. 17 and 21 are diagrams that illustrate embodiments which use pressure wave velocity measurement systems. In FIG. 17, an apparatus 144 has a device for measuring the velocity of a high-frequency pressure oscillation along the artery comprising exciter 146 and detector 148. The system also includes a cuff 78 for applying external pressure to the artery, a cuff engine 74 to inflate the cuff 78 to a predetermined pressure, and a processor 80 to control the cuff engine 74 and capture and process the velocity signal.

The propagation velocity measuring device measures the velocity of propagation of a high-frequency pressure oscillation along the artery. The pressure oscillation is induced by an exciter 146 at one point in the artery and the propagated pressure oscillation is sensed at another point in the artery by a detector 148. The velocity of the propagation is calculated from the distance between the exciter 146 and the detector 148 and the difference in phase between the excitation and detection points. The velocity of the propagation is related to the arterial pressure. This device is described in much more detail in the below-referenced U.S. patent application Ser. No. 08/228,213 and its CIP's Ser. No. 08/561,923 and Ser. No. 08/556,547. The velocity measurement systems can operate at a variety of oscillation frequencies ranging from 100 to 1000 Hertz.

In a preferred embodiment, the propagation velocity system is placed on the forearm of the patient. The detector 148 is placed over the radial artery on the styloid process of the radial bone. The exciter 146 is placed approximately 5 cm proximal to the detector 148, also over the radial artery. The cuff 78 is wrapped around the patient's arm to cover the exciter 146 and detector 148 of the velocity measurement system. The cuff 78 can alternately be positioned in between the exciter 146 and detector 148.

The velocity of propagation of the high-frequency pressure oscillation is inversely related to the compliance of the artery, because as the artery compliance increases the velocity decreases. Since the arterial compliance has a peak at a transmural pressure of approximately zero, the propagation velocity will have a minimum at this transmural pressure.

The device works as follows. The processor sends a signal to the cuff engine 74 causing the cuff engine 74 to inflate to a predetermined pressure between the systolic and diastolic pressure. This DC cuff pressure could be determined by either a previous blood pressure measurement, from the calibrated prediction of propagation velocity, tonometer or vascular unloading system, or it could be determined iteratively through successive attempts at measuring the pressure with the present invention. The processor then records the signal from the propagation velocity measurement system for at least one cardiac cycle. The processor then determines the time during the cardiac cycle that the velocity was minimum. The time of this minimum velocity is the time when the applied pressure is approximately equal to the arterial pressure once this determination has been made, the cuff 78 can be deflated.

FIG. 18 illustrates the propagation wave velocity in the artery versus the transmural pressure. Note that this curve has a minimum at a transmural pressure of about zero. This means that the output velocity of the propagation wave will have a minimum when the transmural pressure is equal to zero.

FIGS. 19A and 19B are graphs illustrating the operation of the apparatus of FIG. 17. As shown in these graphs, when the arterial pressure is equal to the external pressure, the velocity of propagation will have a minimum value.

FIG. 20 is a flow chart illustrating the use of the apparatus of FIG. 17. In step 152, an exciter and detector 148 are used to produce an indication of the velocity of a pressure wave transferred through the artery. In step 154, an external pressure is applied which is between the systolic and diastolic pressure. In step 156, a minimum of the velocity measurement is used to obtain a time that the transmural pressure is equal to zero.

FIG. 21 is a diagram illustrating an apparatus 158 using an exciter 160 and a detector 162 which are not placed underneath the external pressure cuff. This system is a pressure/volume embodiment. These pressure/volume embodiments require two signals, one that is related to the arterial pressure, and one that is related to the arterial volume. The volume measurement should be taken in the region over which the external pressure is applied. The external pressure should be within the systolic and the diastolic pressure. Another example of a pressure/volume embodiment is discussed above with respect to FIGS. 57.

In the preferred embodiment, the cuff 78 is a standard oscillometric cuff such as that provided by Critikon for their Dinamap product. The cuff engine 74 is capable of inflating the cuff to a pressure up to 300 mmHg, and the pressure transducer 76 should have a range up to 300 mmHg and sufficient sensitivity to measure pressure changes as small as 0.1 mmHg. The processor 80 should be able to capture analog waveforms and perform mathematical computations.

The cuff engine 74 is preferably under the control of the processor 80 and has a valve (not shown) that can seal off the cuff 78 so that the volume of the cuff 78 can be fixed. This valve (not shown) should be under control of the processor 80.

The processor 80 can be a general-purpose computer, such as an IBM PC, with a multi-function input-output board, such as a National Instruments MIO-16 board. Alternately, a custom microprocessor could be used. Communication to the cuff engine can be by a serial connection between the processor and the cuff engine.

The propagation velocity measuring device measures the velocity of propagation of a high-frequency pressure oscillation along the artery. The pressure oscillation is induced by an exciter 160 at one part of the artery and the propagated pressure oscillation is sensed in another point along the artery by detector 162. The velocity of propagation is calculated from the distance between the exciter 160 and detector 162 and the difference in phase between the excitation and detection points.

Pressure wave velocity measurement systems are described in more detail in U.S. patent application Ser. No. 08/228,213 entitled "Apparatus and Method for Measuring an Induced Perturbation to Determine Blood Pressure" filed Apr. 15, 1994 (corresponding to International Publication W095/28126), and its CIP's Ser. No. 08/561,923 entitled "Apparatus and Method for Measuring an Induced Perturbation to Determine a Physiological Parameter" and Ser. No. 08/556,547 entitled "Apparatus and Method for Measuring an Induced Perturbation to Determine a Physiological Parameter," which are incorporated herein by reference. These systems sometimes have amplitude indications which are available to obtain viscosity information as well.

In a preferred embodiment, the velocity measurement system could be placed over the radial artery on the forearm. The cuff can be wrapped around the wrist, just distal to the exciter.

This embodiment works as follows. The processor sends a signal to the cuff engine to inflate the cuff to some value between the systolic and diastolic pressure. This DC cuff pressure could be determined by a previous blood pressure measurement, from the calibrated prediction of propagation velocity, tonometer or vascular unloading system, or it can be determined iteratively through successive attempts at measuring the pressure with the present invention. Once the pressure in the cuff has been established, the cuff engine closes the valve that seals off the cuff, fixing the volume of air in the cuff.

With the cuff volume fixed, the pressure in the cuff will have a small pulsatile component that is related to the volume of the artery. The DC component of the cuff pressure can be removed by the processor, leaving the pulsatile component. This pulsatile component is related to the volume of the artery.

The processor simultaneously records the pulsatile portion of the cuff pressure and the propagation velocity. These two signals correspond to the volume-indicative signal and the pressure-indicative signal. The processor then determines the slope of the relationship between volume- and pressure-indicative signals by taking the difference between successive pairs of measurements. This slope is related to the compliance and is defined as $$C(k) = \frac{V(k) - V(k-1)}{P(k) - P(k-1)}$$

where V(k) is the volume-indicative signal at sample k, and P(k) is the pressure-indicative signal at sample k.

The time at which this quantity peaks is the time at which the applied pressure is approximately equal to the arterial pressure. Once the peak in compliance is found, the cuff pressure can be set to zero.

FIGS. 22A–D are graphs which illustrate the workings of the embodiment of FIG. 21. In FIG. 22B, the graph of the measured velocity is shown. Looking again at FIG. 21, the pressure wave velocity is measured in a region with no external pressure applied. This means that, as shown in FIG. 18, the transmural pressure will be equal to the arterial pressure, which ranges, for example, from about 80 mmHg to 120 mmHg. Thus the measured velocity will be proportional to the arterial pressure. The measured volume shown in FIG. 22C is measured in a pressure regime where an external pressure is applied by a cuff and where the external pressure is between the systolic and diastolic pressure. This means that the volume signal of FIG. 22C has at least one point where the transmural pressure is equal to zero. In a similar fashion to that described with respect to FIGS. 6A–D, a graph of the measured volume versus measured velocity can be produced. This graph will have the greatest rate of change at a measured velocity $Vel_x$, associated with a time $T_x$, at which the transmural pressure under the cuff is equal to zero or the arterial pressure everywhere is equal to the external applied cuff pressure. The known arterial pressure at measured velocity $Vel_x$ can be used to calibrate the velocity/arterial-pressure curve.

FIG. 23 is a diagram showing apparatus 158 that illustrates an embodiment based upon the arterial closing pressures. In the embodiment shown in FIG. 23, an exciter 60 under the control of an oscillator 162 produces an excitation signal which is passed down the artery and detected by detector 164. The output of detector 164 is filtered, in the manner described in "Apparatus and Method for Measuring an Induced Perturbation to Determine Blood Pressure" International Publication WO 95/28126, to determine the portion of the high-frequency signal that passes through the artery. This filter removes the detected high-frequency components that pass through tissue other than the artery. Processor 80 uses the output of detector 164 to determine whether the artery is closed.

FIGS. 24A–C illustrate the operation of the embodiment shown in FIG. 23. FIG. 24A illustrates the arterial pressure. FIG. 24B illustrates the high-frequency components of the excitation onto the artery that is caused by the exciter 160. FIG. 24C illustrates the high-frequency component of the pressure wave passing through the artery to detector 164. Note that, at an artery closing pressure, the signal is reduced to zero or severely attenuated. The processor 80 can then determine that, at time $T_1$, the transmural pressure is at the transmural pressure that causes the artery to close. Thus, the arterial pressure at time $T_1$ is the cuff pressure plus the artery closing transmural pressure. In this manner, the arterial pressure at a given time can be determined.

The pressure can be can be applied in a variety of locations: over the detector or exciter; in the propagation region; just before the exciter or just after the detector. The different placements will show different responses in the propagated signal (positioning the pressure at the detector, in the propagation region or at the exciter will show attenuation, while positioning the pressure before the exciter or after the detector will show amplification because of reflections), but all could potentially be used to detect opening and/or closing.

FIG. 25 is a diagram illustrating an alternate embodiment of the present invention that operates to determine the time that an artery is opened or closed. In the embodiment shown in FIG. 25, a detector 166 is used to detect the arterial pulse signal.

FIGS. 26A–B are graphs illustrating the operation of the embodiment of FIG. 25. FIG. 26A illustrates the arterial pressure. FIG. 26B illustrates the pulse signal detected at detector 166. At an artery closing pressure, the signal is reduced to zero or severely attenuated. The processor 80 determines, at time $T_1$, the transmural pressure is at the artery closing transmural pressure. In this manner, the arterial pressure at a given time can be determined. The pressure can be applied over the detector or before the detector.

FIG. 27 is a diagram of an apparatus 170 of the present invention using a plethysmograph to obtain an arterial volume indicative signal in two different cardiac cycles with two different external pressures. One of the external pressures is less than the diastolic pressure and the other transmural pressure is between the diastolic and the systolic pressure.

FIG. 28 is a graph illustrating the relationship between arterial volume and the transmural pressure.

FIGS. 29A–C are graphs illustrating the operation of the embodiment of FIG. 27. FIG. 29A illustrates the arterial pressure. At time $T_o$, the external pressure is set at 70 mmHg, a pressure below the diastolic. At time $T_L$, the external pressure is set at 90 mmHg, a pressure between the diastolic and the systolic pressure. FIG. 29B shows volume-indicative signals from the plethysmograph. The top curve is the arterial volume-indicative measurement at a cuff pressure of 70 mmHg starting at time $T_o$. The bottom curve is the arterial volume-indicative measurement at a cuff pressure of 90 mmHg starting at time $T_L$. The processor 80 stores the arterial volume-indicative measurements to compare measurements made at different cycles. Note that the arterial volume measurements are relatively linearly related from time $+T_1$ to time $+T_2$, this range corresponding to the arterial pressures above 90 mmHg. When the arterial pressures go below 90 mmHg, the volume-indicative output of the measurements starting at time $T_L$ drops sharply. As shown in FIG. 29C, the volume indications at different external pressures can be graphed against each other by the processor 80. A linear region of this graph corresponds to the region between time $+T_1$ and time $+T_2$. A nonlinear region of this graph corresponds to the region between time $+T_2$ and time $+T_3$. The time that the arterial pressure equals the external pressure (90 mmHg) can be determined from this graph by processor 80. There is a change in the slope at the point that the transmural pressure is equal to zero. Note that it is also possible to use such a system with two plethysmographs, one having an external applied pressure and the other not.

Various details of the implementation and method are merely illustrative of the invention. It will be understood that various changes in such details may be within the scope of the invention, which is to be limited only by the appended claims. For instance, as discussed above, the present invention could use a relationship between the viscosity and a critical pressure (such as a transmural pressure equal to zero) to determine a blood pressure at a certain time. Or the detector could be placed in a location which would allow it to receive pressures which pass through not only the artery, but skin, muscle, bone, or other tissue. Alternately, for the induced signal cases, a non-linear transfer function, such as the arterial volume versus transmural pressure, can be used to produce harmonics which can be detected using a bandpass filter set at a multiple of the input frequency, to give a signal that could give information about a critical transmural pressure.

Additionally, measurement of the actual flow of the blood can be done with a Doppler flow detector. The blood flow is related to the arterial volume and pressure in such a manner that there is a critical value that can be detected as an event.

What is claimed is:

1. A measurement device for generating an arterial volume indicative signal, the measurement device comprising:
   an exciter adapted to receive an oscillating signal and generate a pressure wave based at least in part on the oscillating signal on the artery at a measurement site on a patient, wherein the pressure wave comprises a frequency; and
   a detector placed sufficiently near the measurement site to detect a volumetric signal indicative of arterial volume of the patient, wherein the volumetric signal comprises an amplitude, and wherein the measurement device is connected to a processor, which determines when the amplitude of the volumetric signal is greatest, thereby determining when transmural pressure is about zero.

2. The measurement device of claim 1, further comprising an oscillator adapted to generate the oscillating signal.

3. The measurement device of claim 1, wherein the measurement device is in communication with a processor.

4. The measurement device of claim 1, wherein the frequency is about 40 Hz.

5. The measurement device of claim 1, wherein the measurement device is in communication with an external pressure application device and the detector comprises a pressure transducer.

6. The measurement device of claim 1, wherein the detector comprises a plethysmograph.

7. The measurement device of claim 1, wherein the exciter comprises an audio transducer.

8. A method of determining the blood pressure of a patient from an arterial volume indicative signal, the method comprising:
   inducing a high-frequency pressure wave onto an artery
   detecting a signal indicative of arterial volume, wherein the signal includes a high-frequency component from the pressure wave;
   filtering low-frequency components from the signal, thereby providing a filtered signal, wherein the filtered signal comprises an amplitude; and
   determining when the amplitude of the filtered signal is greatest, thereby determining when transmural pressure is about zero.

9. The method of claim 8, wherein the filtering is performed digitally.

10. The method of claim 8, wherein the signal is detected with a plethysmograph.

11. The method of claim 8, further comprising changing the pressure induced onto the artery by an external pressure application device to determine systolic and diastolic blood pressure.

12. The method of claim 8, further comprising changing the pressure induced onto the artery by an external pressure application device to ensure the pressure induced is between systolic and diastolic blood pressure.

13. A measurement device for determining the blood pressure of a patient by finding a time when transmural pressure is approximately equal to zero, the measurement device comprising:

a device, which perturbs at least one of pressure and volume of an artery of a patient; and a pressure transducer placed sufficiently near a measurement site to detect a signal indicative of an oscillation response when the device perturbs the at least one of pressure and volume, wherein the measurement device is in communication with a processor, which determines when an amplitude of the signal is greatest, thereby determining the time when transmural pressure is approximately equal to zero.

14. A measurement device for determining the blood pressure of a patient, the measurement device comprising:

an exciter, which induces a pressure oscillation along an artery; and a detector, which senses the pressure oscillation and outputs a signal indicative of the pressure oscillation, wherein at least one of the exciter and detector are adapted to be placed between portions of an external pressure application device and a measurement site, wherein the measurement device is in communication with a processor, which determines a time when an amplitude of the signal is greatest, and determine a point where transmural pressure is about zero based at least in part upon the time.

15. The measurement device of claim 14, further comprising an oscillator.

16. A method of determining blood pressure of a patient, the method comprising:

providing a range of pressures to an artery;

providing an oscillating signal to the artery;

measuring a signal indicative of the oscillating signal and at least one pressure within the range of pressures;

filtering the signal indicative of the oscillating signal and at least one pressure within the range of pressures to produce a filtered signal, wherein the filtered signal comprises an amplitude;

determining a point of about zero transmural pressure when the amplitude of the filtered signal is at maximum; and determining a pressure within the range in pressures based at least in part from said point of about zero transmural pressure.

17. A method of determining blood pressure of a patient, the method comprising:

detecting a signal indicative of an oscillation along an artery; and determining a point of zero transmural pressure from an amplitude maximum of said detected signal.

18. A measurement device for generating an arterial volume indicative signal, the measurement device comprising:

an exciter adapted to receive an oscillating signal and generate a pressure wave based at least in part on the oscillating signal of the artery at a measurement site on a patient, wherein the pressure wave comprises a frequency;

a detector placed sufficiently near the measurement site to detect a volumetric signal indicative of arterial volume of the patient; and a high pass filter, which substantially removes pulsatile components from the volumetric signal, thereby producing a filtered signal, wherein the filtered signal comprises an amplitude, and wherein the measurement device is in communication with a processor, which determines when the amplitude of the filtered signal is greatest, thereby determining when transmural pressure is about zero.

19. A measurement device for generating an arterial volume indicative signal, the measurement device comprising:

an exciter adapted to receive an oscillating signal and generate a pressure wave based at least in part on the oscillating signal on the artery at a measurement site on a patient, wherein the pressure wave comprises a frequency; and a detector placed sufficiently near the measurement site to detect a volumetric signal indicative of arterial volume of the patient; wherein the measurement device is in communication with a processor, which digitally filters the volumetric signal, thereby producing a filtered signal, wherein the filtered signal comprises an amplitude, and wherein the processor, determines when the amplitude of the filtered signal is greatest, thereby determining when transmural pressure is about zero.

* * * * *

UNITED STATES PATENT AND TRADEMARK OFFICE
CERTIFICATE OF CORRECTION

| | | |
|---|---|---|
| PATENT NO. | : 6,939,305 B2 | Page 1 of 1 |
| APPLICATION NO. | : 10/685068 | |
| DATED | : September 6, 2005 | |
| INVENTOR(S) | : Bryan P. Flaherty, Mark H. Sher and Richard G. Caro | |

It is certified that error appears in the above-identified patent and that said Letters Patent is hereby corrected as shown below:

On the title page item (73), line 1, delete "Irvine, CA (US)" and insert -- 40 Parker Irvine, CA (US) 92618 --, therefor.

On the title page item (56), under (Other Publications) at line 1, delete "al.;" and insert -- al., --, therefor.

In column 12 at line 51, delete "pressure" and insert -- pressure. --, therefor.

In column 12 at line 51, delete "once" and insert -- Once --, therefor.

In column 15 at line 3, after "can be" delete "can be".

In column 16 at line 46, in claim 8, after "artery" insert -- ; --.

In column 18 at line 13, in claim 18, delete "of" and insert -- on --, therefor.

Signed and Sealed this

Nineteenth Day of September, 2006

JON W. DUDAS
*Director of the United States Patent and Trademark Office*